(12) United States Patent
Armstrong et al.

(10) Patent No.: US 10,835,397 B2
(45) Date of Patent: Nov. 17, 2020

(54) LATTICE

(71) Applicant: W. L. Gore & Associates, Inc., Newark, DE (US)

(72) Inventors: Joseph R. Armstrong, Flagstaff, AZ (US); Edward H. Cully, Flagstaff, AZ (US); Jeffrey B. Duncan, Flagstaff, AZ (US); Mark Y. Hansen, Flagstaff, AZ (US); William D. Montgomery, Flagstaff, AZ (US); Wendy J. Terry, Flagstaff, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/491,435

(22) Filed: Apr. 19, 2017

(65) Prior Publication Data

US 2017/0216062 A1 Aug. 3, 2017

Related U.S. Application Data

(63) Continuation of application No. 13/675,959, filed on Nov. 13, 2012, which is a continuation-in-part of
(Continued)

(51) Int. Cl.
*A61F 2/82* (2013.01)
*A61F 2/915* (2013.01)
(Continued)

(52) U.S. Cl.
CPC ............... *A61F 2/915* (2013.01); *A61F 2/06* (2013.01); *A61F 2/07* (2013.01); *A61F 2/82* (2013.01);
(Continued)

(58) Field of Classification Search
CPC ...................................................... A61F 2/82
See application file for complete search history.

(56) References Cited

U.S. PATENT DOCUMENTS 3,953,566 A 4/1976 Gore
4,187,390 A 2/1980 Gore
(Continued)

FOREIGN PATENT DOCUMENTS

CA 2462509 A1 4/2003
CN 101926699 A 12/2010
(Continued)

OTHER PUBLICATIONS

International Search Report and Written Opinion for PCT/US2014/068430 dated Feb. 20, 2015, corresponding to U.S. Appl. No. 14/558,296, 9 pages.

(Continued)

*Primary Examiner* — Matthew W Schall

(57) ABSTRACT

The invention relates to medical devices and methods of using them. The devices are prostheses which can be percutaneously deliverable with (or on) an endovascular catheter or via other surgical or other techniques and then expanded. The prostheses are configured to have a lattice resistant to dilation and creep, which is defined by a plurality of openings. The prosthesis may also optionally have a stent disposed proximal to the lattice. In exemplary embodiments, the fluoropolymer is expanded polytetrafluoroethylene. The composite materials exhibit high elongation while substantially retaining the strength properties of the fluoropolymer membrane. In at least one embodiment, the lattice is made of a composite material that includes a least one fluoropolymer membrane including serpentine fibrils and an elastomer. A lattice including a generally tubular member formed of a composite material including a least one fluoropolymer
(Continued)

membrane containing serpentine fibrils and an elastomer is also provided.

17 Claims, 20 Drawing Sheets

Related U.S. Application Data application No. 13/298,060, filed on Nov. 16, 2011, now Pat. No. 9,839,540.

(60) Provisional application No. 61/598,828, filed on Feb. 14, 2012, provisional application No. 61/523,115, filed on Aug. 12, 2011, provisional application No. 61/433,069, filed on Jan. 14, 2011.

(51) Int. Cl.
*A61F 2/88* (2006.01)
*A61F 2/89* (2013.01)
*A61F 2/06* (2013.01)
*A61F 2/07* (2013.01)
*A61F 2/90* (2013.01)

(52) U.S. Cl.
CPC .................. *A61F 2/88* (2013.01); *A61F 2/89* (2013.01); *A61F 2/90* (2013.01); *A61F 2002/075* (2013.01); *A61F 2002/91558* (2013.01); *A61F 2002/91583* (2013.01); *A61F 2210/0076* (2013.01); *A61F 2220/005* (2013.01); *A61F 2220/0033* (2013.01); *A61F 2230/001* (2013.01); *A61F 2250/0039* (2013.01); *A61F 2250/0048* (2013.01); *A61F 2250/0067* (2013.01); *A61F 2250/0071* (2013.01)

(56) References Cited

U.S. PATENT DOCUMENTS

| | | |
|---|---|---|
| 4,332,035 A | 6/1982 | Mano |
| 4,877,661 A | 10/1989 | House et al. |
| 4,955,899 A | 9/1990 | Della Coma et al. |
| 5,026,513 A | 6/1991 | House et al. |
| 5,071,609 A | 12/1991 | Tu et al. |
| 5,476,589 A | 12/1995 | Bacino |
| 5,534,007 A | 7/1996 | St. Germain et al. |
| 5,549,663 A | 8/1996 | Cottone et al. |
| 5,673,102 A | 9/1997 | Suzuki et al. |
| 5,708,044 A | 1/1998 | Branca |
| 5,718,973 A | 2/1998 | Lewis et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell |
| 5,853,419 A | 12/1998 | Imran |
| 5,925,061 A | 7/1999 | Ogi et al. |
| 5,935,162 A | 8/1999 | Dang |
| 6,010,529 A | 1/2000 | Herweck et al. |
| 6,013,854 A | 1/2000 | Moriuchi |
| 6,042,588 A | 3/2000 | Munsinger et al. |
| 6,042,605 A | 3/2000 | Martin et al. |
| 6,042,606 A | 3/2000 | Frantzen |
| 6,174,329 B1 | 1/2001 | Callol et al. |
| 6,190,406 B1 | 2/2001 | Duerig et al. |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,488,701 B1 | 12/2002 | Nolting et al. |
| 6,541,589 B1 | 4/2003 | Baillie |
| 6,620,190 B1 | 9/2003 | Colone |
| 6,626,939 B1 | 9/2003 | Burnside et al. |
| 6,673,102 B1 | 1/2004 | Vonesh et al. |
| 6,673,107 B1 | 1/2004 | Brandt et al. |
| 6,730,120 B2 | 5/2004 | Berg et al. |
| 6,755,856 B2 | 6/2004 | Fierens et al. |
| 6,758,858 B2 | 7/2004 | McCrea et al. |
| 6,890,350 B1 | 5/2005 | Walak |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,306,729 B2 | 12/2007 | Bacino et al. |
| 7,419,678 B2 | 9/2008 | Falotico |
| 7,531,611 B2 | 5/2009 | Sabol et al. |
| 7,789,908 B2 | 9/2010 | Sowinski et al. |
| 7,811,314 B2 | 10/2010 | Fierens et al. |
| 7,815,763 B2 | 10/2010 | Fierens et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 8,585,753 B2 | 11/2013 | Scanlon et al. |
| 9,345,601 B2 | 5/2016 | Jantzen et al. |
| 9,737,422 B2 | 8/2017 | Armstrong et al. |
| 9,795,496 B2 | 10/2017 | Armstrong et al. |
| 9,839,540 B2 | 12/2017 | Armstrong et al. |
| 9,931,193 B2 | 4/2018 | Cully et al. |
| 10,166,128 B2 | 1/2019 | Armstrong et al. |
| 10,279,084 B2 | 5/2019 | Goepfrich et al. |
| 10,335,298 B2 | 7/2019 | Armstrong et al. |
| 10,507,124 B2 | 12/2019 | Armstrong et al. |
| 2001/0053929 A1 | 12/2001 | Vonesh et al. |
| 2002/0076542 A1 | 6/2002 | Kramer et al. |
| 2002/0198588 A1 | 12/2002 | Armstrong et al. |
| 2003/0055494 A1 | 3/2003 | Bezuidenhout et al. |
| 2003/0060871 A1 | 3/2003 | Hill et al. |
| 2003/0180488 A1 | 9/2003 | Lim et al. |
| 2004/0024442 A1 | 2/2004 | Sowinski et al. |
| 2004/0024448 A1 | 2/2004 | Chang et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0224442 A1 | 11/2004 | Grigg |
| 2004/0260277 A1 | 12/2004 | Maguire |
| 2005/0080476 A1 | 4/2005 | Gunderson et al. |
| 2005/0137680 A1 | 6/2005 | Ortiz et al. |
| 2005/0283224 A1 | 12/2005 | King |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0106337 A1 | 5/2006 | Blankenship |
| 2006/0118236 A1 | 6/2006 | House et al. |
| 2006/0135985 A1 | 6/2006 | Cox et al. |
| 2006/0161241 A1 | 7/2006 | Barbut et al. |
| 2006/0190070 A1 | 8/2006 | Dieck et al. |
| 2006/0259133 A1 | 11/2006 | Sowinski et al. |
| 2006/0271091 A1 | 11/2006 | Campbell et al. |
| 2006/0276883 A1 | 12/2006 | Greenberg et al. |
| 2007/0012624 A1 | 1/2007 | Bacino et al. |
| 2007/0060999 A1 | 3/2007 | Randall et al. |
| 2007/0129786 A1 | 6/2007 | Beach et al. |
| 2007/0207186 A1 | 9/2007 | Scanlon et al. |
| 2007/0207816 A1 | 9/2007 | Spain |
| 2007/0208421 A1 | 9/2007 | Quigley |
| 2007/0213800 A1 | 9/2007 | Fierens et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0051876 A1 | 2/2008 | Ta et al. |
| 2008/0097301 A1 | 4/2008 | Alpini et al. |

(56) References Cited

U.S. PATENT DOCUMENTS

| | | |
|---|---|---|
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault De La Menardiere et al. |
| 2009/0104247 A1 | 4/2009 | Pacetti |
| 2009/0182413 A1 | 7/2009 | Burkart et al. |
| 2009/0306766 A1 | 12/2009 | McDermott et al. |
| 2010/0016940 A1 | 1/2010 | Shokoohi et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Clough |
| 2010/0256738 A1 | 10/2010 | Berglund |
| 2010/0286760 A1 | 11/2010 | Beach et al. |
| 2010/0305682 A1 | 12/2010 | Furst |
| 2011/0009953 A1 | 1/2011 | Luk et al. |
| 2011/0087318 A1 | 4/2011 | Daugherty et al. |
| 2012/0323211 A1 | 12/2012 | Ogle et al. |
| 2013/0131780 A1 | 5/2013 | Armstrong et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0253466 A1 | 9/2013 | Campbell et al. |
| 2013/0297003 A1 | 11/2013 | Pinchuk |
| 2014/0135897 A1 | 5/2014 | Cully et al. |
| 2014/0172066 A1 | 6/2014 | Goepfrich et al. |
| 2014/0180402 A1 | 6/2014 | Bruchman et al. |
| 2015/0005870 A1 | 1/2015 | Kovach et al. |
| 2015/0157770 A1 | 6/2015 | Cully et al. |
| 2015/0313871 A1 | 11/2015 | Li et al. |
| 2016/0015422 A1 | 1/2016 | De Cicco et al. |
| 2017/0065400 A1 | 3/2017 | Armstrong et al. |
| 2017/0216062 A1 | 8/2017 | Armstrong et al. |
| 2018/0177583 A1 | 6/2018 | Cully et al. |
| 2019/0125517 A1 | 5/2019 | Cully et al. |
| 2019/0209739 A1 | 7/2019 | Goepfrich et al. |
| 2019/0216592 A1 | 7/2019 | Cully et al. |

FOREIGN PATENT DOCUMENTS

| | | |
|---|---|---|
| EP | 0293090 A2 | 11/1988 |
| EP | 0313263 A2 | 4/1989 |
| EP | 0775472 A2 | 5/1997 |
| EP | 0815806 A2 | 1/1998 |
| EP | 0893108 A2 | 1/1999 |
| EP | 1666003 A1 | 6/2006 |
| EP | 2255750 A2 | 12/2010 |
| JP | 02-000645 A | 1/1990 |
| JP | H09241412 A | 9/1997 |
| JP | H11290448 A | 10/1999 |
| JP | 11-512635 A | 11/1999 |
| JP | 2001509702 A | 7/2001 |
| JP | 2007-526098 A | 9/2007 |
| JP | 2008-506459 A | 3/2008 |
| JP | 2010-500107 A | 1/2010 |
| JP | 2010504174 A | 2/2010 |
| JP | 2010535075 A1 | 11/2010 |
| RU | 2124986 C1 | 1/1999 |
| WO | 94/13224 A1 | 6/1994 |
| WO | WO9416802 A1 | 8/1994 |
| WO | WO9505555 A1 | 2/1995 |
| WO | WO9607370 A1 | 3/1996 |
| WO | 1996040348 A1 | 12/1996 |
| WO | WO9710871 A1 | 3/1997 |
| WO | 1999026558 A1 | 6/1999 |
| WO | WO0041649 A1 | 7/2000 |
| WO | WO0047271 A1 | 8/2000 |
| WO | 01/64278 A1 | 9/2001 |
| WO | WO0174272 A2 | 10/2001 |
| WO | WO02060506 A1 | 8/2002 |
| WO | 2003003946 A1 | 1/2003 |
| WO | 2004000375 A1 | 12/2003 |
| WO | 2006019626 A2 | 2/2006 |
| WO | 2006058322 A2 | 6/2006 |
| WO | 2008021002 A1 | 2/2008 |
| WO | 2008028964 A2 | 3/2008 |
| WO | 2008036870 A2 | 3/2008 |
| WO | 2008049045 A2 | 4/2008 |
| WO | 2008/097589 A1 | 8/2008 |
| WO | 2009017827 A1 | 2/2009 |
| WO | 2009100210 A1 | 8/2009 |
| WO | 2009108355 A1 | 9/2009 |
| WO | 2010006783 A1 | 1/2010 |
| WO | 2010008570 A1 | 1/2010 |
| WO | 2010030766 A1 | 3/2010 |
| WO | 2010132707 A1 | 11/2010 |
| WO | 2010150208 A2 | 12/2010 |
| WO | 2011098565 A1 | 8/2011 |
| WO | 2012/011261 A1 | 1/2012 |
| WO | 2012099979 A1 | 7/2012 |
| WO | 2012/158944 A1 | 11/2012 |
| WO | 2013/074663 A2 | 5/2013 |
| WO | 2013109337 A1 | 7/2013 |

OTHER PUBLICATIONS

International Search Report and Written Opinion issued in PCT/US2011/061165, dated Oct. 1, 2012, 20 pages.

International Search Report and Written Opinion issued in PCT/US2012/064908, dated Feb. 4, 2013, 10 pages.

International Search Report and Written Opinion issued in PCT/US2012/066518, dated Feb. 4, 2013, 10 pages.

International Search Report and Written Opinion issued in PCT/US2012065066, dated Nov. 11, 2013, 9 pages.

International Search Report and Written Opinion issued in PCT/US2016/028671, dated Jul. 28, 2016, 19 pages.

International Search Report issued in PCT/US2014/013496, dated Dec. 2, 2014, 3 pages.

Nlishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

Extended European Search Report issued in EP Application No. 17186750.0, dated Oct. 24, 2017, 7 pages.

International Preliminary Report on Patentability issued in PCT/US2016/028671, dated Nov. 1, 2018, 12 pages.

International Preliminary Report on Patentability received for PCT Patent Application No. PCT/US11/61165, dated Jul. 25, 2013, 14 pages.

International Preliminary Report on Patentability received for PCT Patent Application No. PCT/US12/65066, dated May 30, 2014, 14 pages.

International Search Report and Written Opinion for PCT/US2014/068430 dated Feb. 20, 2015, corresponding to U.S. Appl. No. 14/558,296, 9 pages.

International Search Report and Written Opinion issued in PCT1US20121064908, dated Feb. 4, 2013, 10 pages.

International Search Report and Written Opinion issued in PCT1US2012065066, dated Nov. 11, 2013, 9 pages.

International Search Report and Written Opinion issued in PCT1US20161028671, dated Jul. 28, 2016, 19 pages.

International Search Report for PCT/US2014/013496 dated Dec. 2, 2014, corresponding to U.S. Appl. No. 13/755,481, 4 pages.

International Search Report issued in PCT/US2013/076405, dated May 6, 2014, 7 pages.

International Written Opinion received for PCT Patent Application No. PCT/US2014/013496, dated Dec. 2, 2014, 5 pages.

Nakayama, Yasuhide. Microporous Stent Achieves Brain Aneurysm Occlusion Without Disturbing Branching Flow. NeuroNews Nov. 2012; 8:1-2.

Partial International Search Report for PCT/US2012/065066, dated Jul. 1, 2013, corresponding to U.S. Appl. No. 13/675,959, 3 pages.

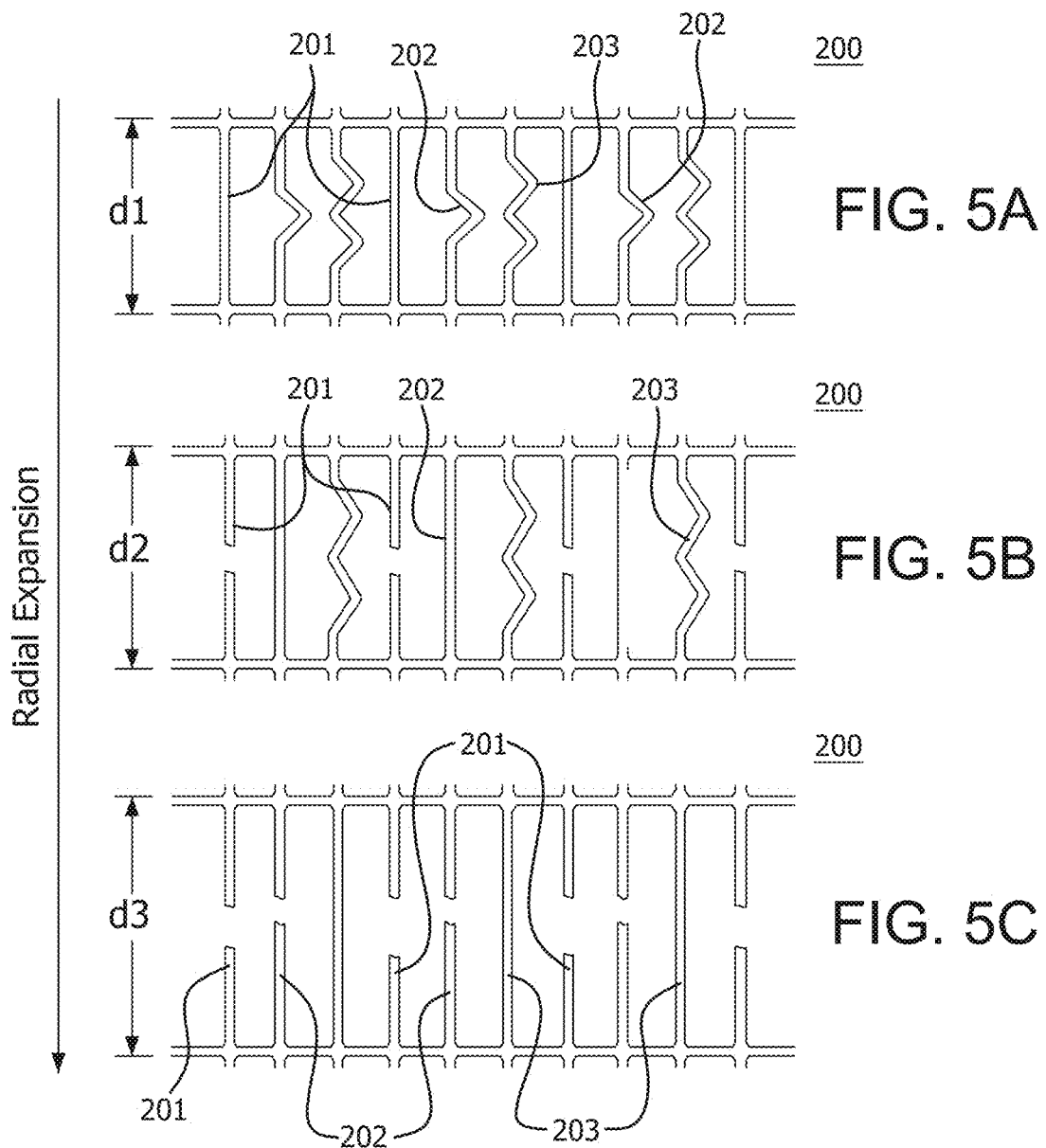

Axial Expansion →

LATTICE

CROSS-REFERENCE TO A RELATED APPLICATION

This application is a continuation of U.S. patent application Ser. No. 13/675,959, filed on Nov. 13, 2012, which claims priority to U.S. Patent Application No. 61/598,828 filed on Feb. 14, 2012, and is a Continuation-In-Part of U.S. patent application Ser. No. 13/298,060 filed on Nov. 16, 2011, which, in turn, claims priority under 35 U.S.C. 119(e) to U.S. Provisional Application No. 61/433,069 filed on Jan. 14, 2011 and U.S. Provisional Application No. 61/523,115 filed on Aug. 12, 2011, the contents of all noted applications are incorporated herein in their entireties.

FIELD OF THE INVENTION

The invention relates generally to medical implants for supporting, maintaining, or repairing a lumen, passageway or opening in a living body and to methods of using them. In particular, the invention relates to medical devices that are designed to be inserted endoluminally into a body.

BACKGROUND OF THE INVENTION

Medical stents are generally known. One use for medical stents is to expand a body lumen, such as a blood vessel, which has contracted in diameter through, for example, the effects of lesions called atheroma or the occurrence of cancerous tumors. Atheroma refers to lesions within arteries that include plaque accumulations that can obstruct blood flow through the vessel. Over time, the plaque can increase in size and thickness and can eventually lead to clinically significant narrowing of the artery, or even complete occlusion. When expanded against the body lumen, which has contracted in diameter, the medical stents provide a tube-like support structure inside the body lumen. Stents, in combination with coverings, also can be used for the endovascular repair of aneurysms, an abnormal widening or ballooning of a portion of a body lumen which can be related to weakness in the wall of the body lumen. Various stent designs are known in the art. Stents typically are tubular, and are expandable or self-expand from a relatively small diameter to a larger diameter.

SUMMARY OF THE INVENTION

A prosthesis according to this application is suitable for implantation into various body vessels or openings and can be adjusted in accordance to the size (length or diameter) of said body vessel or opening. Further, the prosthesis in accordance with the instant invention is an endovascular prosthesis resistant to dilation and creep that can be configured to radially or longitudinally expand under the action of the distensive force in a sloped or in a stepped manner. The prosthesis is provided with or without one or more stents, one or more grafts, or a combination of stents and grafts.

In one embodiment, a prosthesis is provided with a lattice, which defines a plurality of openings. The lattice is resistant to dilation and creep and can be configured to radially expand under the action of the distensive force in a sloped or in a stepped manner. The lattice comprises at least two circumferential segments. The circumferential segments are oriented at an angle of between about 45° and about 90° with respect to the longitudinal axis of the prosthesis. When not compacted the prosthesis and lattice expands radially into an enlarged first diametrical dimension, wherein the full expansion of the prosthesis is constrained by the lattice. At least one circumferential segment of the lattice is resistant to further expansion. The prosthesis and lattice can be adjusted to a further enlarged second diametrical dimension when distensive force is applied to the lattice and the circumferential segment resistant to further expansion is plastically deformed (i.e. stretch with little or no recoil) or ruptured. If the circumferential segment is plastically deformed, the lattice expands in a sloped manner. If the circumferential segment ruptures, the lattice expands in a stepped manner. Once the prosthesis expands radially into an enlarged second diametrical dimension, at least one circumferential segment of the lattice is resistant to further expansion. An embodiment comprises at least two continuous longitudinal segments, and at least two continuous circumferential segments, wherein the longitudinal and circumferential segments define the plurality of openings. In such an embodiment, the longitudinal segments are substantially parallel to a longitudinal axis of the prosthesis.

In another embodiment, a prosthesis has a lattice that can be configured to longitudinally expand under the action of the distensive force in a sloped or in a stepped manner in which longitudinal segments are plastically deformed or ruptured. In another embodiment, said prosthesis has a lattice that can be configured to radially and longitudinally expand.

In another embodiment, a prosthesis has a multi-layer lattice, which defines a plurality of openings. The lattice is resistant to dilation and creep and can be configured to radially expand under the action of the distensive force in a sloped or in a stepped manner. The lattice forms a unitary tubular structure having a first expanded diameter when the prosthesis is not radially constrained. At least one layer within the lattice is under load when the prosthesis is not radially constrained. Such layer is resistant to further radial expansion of the prosthesis. The prosthesis can be adjusted to a second expanded diameter that is greater than the first diameter when a distensive force is applied to the lattice. At a prescribed pressure, the distensive force causes the layer of the lattice that is resistant to further radial expansion of the prosthesis to rupture or plastically deform. If the layer is plastically deformed, the lattice expands in a sloped manner. If the layer is ruptured, the lattice expands in a stepped manner. The lattice then expands radially to the second expanded diameter. At least one layer within the lattice is under load at the second expanded diameter. Such layer is resistant to further radial expansion of the prosthesis. The number of layers having varied expanded diameters within the lattice is not particularly limited. The expansion using the distensive force with prescribed pressure can continue to rupture or plastically deform individual layers or several layers at the same time if they all have the same expanded diameter until all the layers are ruptured or plastically deformed and the indwelling prosthesis is allowed to achieve its full, unconstrained diameter. Alternatively, the prosthesis can reach a built in "hard-stop" at which point no further expansion is allowed by the lattice.

In another embodiment, a prosthesis has a multi-layer lattice that can be configured to longitudinally expand in either a stepped or a sloped manner, yet resist dilation or creep. In another embodiment, a prosthesis has a multi-layer lattice that can be configured to radially and/or longitudinally expand. In another embodiment, a prosthesis has a multi-layer lattice that can be configured to radially and/or longitudinally expand in partially stepped and partially sloped manner in which, for example, the segments in one layer are broken and the segments in another layer are plastically deformed.

In another embodiment, a prosthesis is an accessory prosthesis having a lattice with or without a stent frame at one or both ends. The stent frame may be balloon expandable or self-expanding. The lattice defines a plurality of openings and has at least two continuous longitudinal segments and at least two continuous circumferential segments. The lattice can be configured to radially and/or longitudinally expand in a stepped or a sloped manner. The accessory prosthesis can be deployed in a prescribed lumen prior to the deployment of the primary prosthesis and the primary prosthesis can be deployed within it. The function of the accessory prosthesis is to constrain the primary prosthesis at a reduced size, yet allow diametrical adjustment as necessary.

In another embodiment, a prosthesis has a drug eluting lattice. The lattice has at least one layer with a therapeutic agent that is disposed in between two nonpermeable layers. The therapeutic agent is sealed within the lattice between the two nonpermeable layers. The lattice also defines a plurality of openings and the therapeutic agent is sealed within the lattice at the inner walls of the lattice openings. As the prosthesis experiences a distensive force, the nonpermeable layers expand, for instance, radially into an enlarged diametrical dimension, while the inner walls of the openings fail, break, crack or tear to allow the therapeutic agent to be released.

In another embodiment, a prosthesis is provided that is configured to have pulsatile compliance. The prosthesis has a stent (i.e. a self-expanding stent), and can have a distal end and/or proximal end flared such that a diameter at an end of the stent is greater than a diameter defined in the center portion of the stent. The prosthesis further has a lattice defining a plurality of openings. These two components of the prosthesis have large differences in mechanical properties. The lattice can be very elastic or flexible, and the stent is typically very stiff in comparison. Thus, the combination produces an elastic response within the physiological pressure range of a natural vessel such as a blood vessel including for example a diseased blood vessel. In an embodiment, the combination can produce a non-linear elastic response within the physiological pressure range of a natural vessel. This characteristic of pulsatile expansion and contraction of host vessels requires fine mechanical compliance of the prosthesis, i.e., a close mimicking by the prosthetic device of the mechanics and timing of the natural vessel distending and reshaping under change in blood pressure. An elastomeric lattice covering on the outer surface of a stent embodiment provides an elastic constraining force to the stent (i.e. inward force) while the stent can provide an expansion force (i.e. outward force). This can be beneficial in avoiding draping of the lattice covering into the luminal space of the stent while it may additionally provide pulsatile compliance.

In another embodiment, a lattice includes a generally tubular member containing a plurality of openings and a luminal (inner) and exterior (outer) surface. The openings may each have a size of less than about 2.0 mm, 1.0 mm, or even less than 0.5 mm. The generally tubular member comprises a composite material that has an expanded fluoropolymer membrane and preferably an elastomer. The fluoropolymer may be expanded polytetrafluoroethylene. In exemplary embodiments, the expanded fluoropolymer membrane includes serpentine fibrils. In at least one exemplary embodiment, the expanded fluoropolymer membrane may include a plurality of serpentine fibrils.

An embodiment of an endovascular prosthesis can comprise a generally tubular lattice comprising at least two circumferential segments that are oriented at an angle of between about 45 degrees and about 90 degrees with respect to the longitudinal axis of the generally tubular lattice; wherein the generally tubular lattice is adapted to expand radially into an enlarged first diametrical dimension and at least one circumferential segment of the lattice being resistant to further expansion, and wherein the generally tubular lattice can be adjusted to a further enlarged second diametrical dimension when distensive force is applied thereto and the circumferential segment resistant to further expansion is plastically deformed or broken. The lattice can further comprise at least two longitudinal segments that are substantially parallel to the axis of the generally tubular lattice and wherein said at least two longitudinal segments and said at least two circumferential segments define a plurality of openings.

An alternative embodiment of an endovascular prosthesis comprises a lattice defining a plurality of openings; the lattice comprising (ii) at least two circumferential segments that are oriented at an angle of between about 45 degrees and about 90 degrees with respect to the longitudinal axis of the prosthesis; wherein at least one circumferential segment has excess length when the prosthesis expands radially into an enlarged first diametrical dimension and at least one circumferential segment of the lattice being resistant to further expansion.

An embodiment of an endovascular prosthesis can comprise a multi-layer lattice resistant to dilation and creep; each layer of the lattice defines a plurality of openings wherein when the prosthesis expands radially into an enlarged first diametrical dimension and at least one layer of the lattice being resistant to further expansion, and wherein the prosthesis can be adjusted to a further enlarged second diametrical dimension when distensive force is applied thereto and the layer resistant to further expansion is compromised.

Another embodiment of an endovascular prosthesis comprises a lattice defining a plurality of openings and having a generally tubular form; the lattice comprising (i) at least two longitudinal segments that are substantially parallel to a longitudinal axis of the lattice, and (ii) at least two circumferential segments that are oriented at an angle with respect to the longitudinal axis; wherein at least one circumferential or longitudinal segment has an excess length when the lattice expands radially into an enlarged first diametrical dimension or longitudinally into an enlarged first linear dimension and at least one circumferential or longitudinal segment of the lattice being resistant to further expansion.

An embodiment of an endovascular prosthesis having a therapeutic lattice reservoir comprises a lattice having at least two layers nonpermeable to therapeutic agents; and a reservoir layer disposed there between comprising one or more therapeutic agents; the lattice defines a plurality of openings having an inner wall and the therapeutic agent is sealed within the reservoir layer at the inner wall of the openings; wherein as the prosthesis is adjusted to an enlarged diametrical dimension by a distensive force applied thereto, the inner wall of the openings is adapted to be resistant to dilation allowing the therapeutic agent to be released.

An embodiment of an endovascular prosthesis with pulsatile compliance comprises a stent having one or more ends; and a lattice defining a plurality of openings covering the stent; wherein a combination of the stent and the lattice produces an elastic response within a physiological pressure range of a diseased blood vessel.

Another embodiment of a multi-layer lattice endovascular prosthesis comprises a multi-layer lattice resistant to physiological pressures; each layer of the lattice defines a plurality of openings wherein when the prosthesis expands radially into an enlarged first diametrical dimension and at least one layer of the lattice being resistant to further expansion, and wherein the prosthesis can be adjusted to a further enlarged second diametrical dimension when distensive force is applied thereto and the layer resistant to further expansion is compromised.

An embodiment of a lattice comprises a generally tubular member having a plurality of openings therein and a luminal surface and an exterior surface, wherein said member comprises a composite material including a least one fluoropolymer membrane and an elastomer, and wherein said fluoropolymer membrane includes serpentine fibrils.

The devices described herein have various uses. An exemplary use is in a method of treating stenosis in a vessel. For example, the device is a stent with a lattice having an insertion configuration with a reduced profile and a deployed configuration with an enlarged profile greater than the insertion profile. This stent is inserted into the vasculature of the patient. The stent is then positioned and deployed within the vessel.

Numerous variations and modifications of these exemplary prostheses and methods of using them are contemplated. Additional features and advantages of the invention will be set forth in the description or can be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory, and are intended to provide further explanation of the invention as claimed.

BRIEF DESCRIPTION OF THE DRAWINGS

The accompanying drawings are included to provide a further understanding of the invention, and are incorporated in and constitute a part of this specification, illustrate embodiments of the invention, and together with the description serve to explain the principles of the invention.

In the drawings:

FIGS. 5A-5C illustrate a partial close-up of a lattice with circumferential segments of varying length during radial expansion;

DETAILED DESCRIPTION OF THE ILLUSTRATED EMBODIMENTS

Figure 1A:
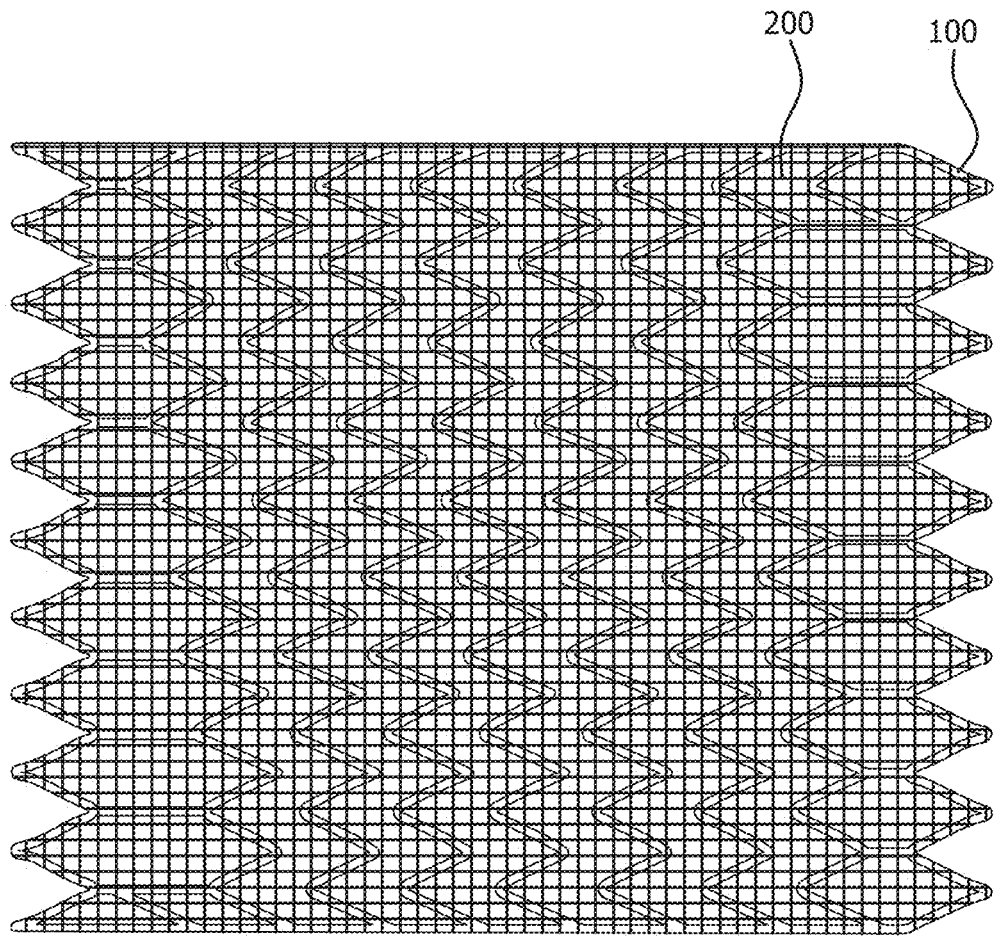
FIG. 1A is a plan view of a stent with a square-shaped lattice covering.

Unless defined otherwise, all technical and scientific terms used herein have the same meaning as commonly understood by one of ordinary skill in the art to which the invention belongs. In the drawings, the thickness of the lines, layers, and regions may be exaggerated for clarity. Like numbers found throughout the figures denote like elements.

A prosthesis is a device adapted to be inserted into a body and then deployed within the body such as within the carotid artery. The prosthesis has a stent with a framework of struts or relatively rigid sections. Alternatively, the prosthesis has a graft with, for example, a flexible, cylindrical tubing supported by a plurality of circumferential ring-like scaffold elements. In yet another alternative, the prosthesis has a stent and a graft to form a stent-graft. Examples of such devices are described in U.S. Pat. No. 6,361,637 to Martin et al. and U.S. Patent Publication 20070198077 to Cully, et al., the entire disclosures of which are incorporated herein by reference. Most generally, prostheses assist in structurally supporting the host vessel lumen, maintaining patency through the vessel, passageway or opening, repairing vessels having an intimal flap or dissection, or isolating sections of a host vessel lumen, such as aneurysms. In another embodiment, said prosthesis are vascular grafts, e.g. GORE-TEX® Vascular Grafts, which are used, inter alia, to create a conduit for repeated blood access during hemodialysis or as conduits between vessels. According to one embodiment of the invention, any of the prosthesis mentioned above can be customized to fit a particular anatomy, including adjusting its length and inside diameters. In another embodiment, said prosthesis can also be tapered along all or a portion of its length so that the inside diameter changes along the length.

Coverings can be provided for a stent, a graft, or a stent-graft. Alternatively, coverings can be used independently. The use of coverings in combination with the stent, the graft, or the stent-graft can help, for example, to minimize or at least reduce the risk of introduction of emboli into a bloodstream, resist tissue encroachment into the lumen defined by the stent, reduce pressure on a weakened part of a blood vessel to reduce the risk of vessel rupture, and/or to create a conduit for attaching at least two vessels. Coverings can be made from continuous materials with no holes visible without magnification.

Various coverings can be provided independently or on the interior or exterior surfaces of the stent, the graft, the stent-graft, or both. A prosthesis embodiment can have a covering attached to the luminal (interior) or exterior surface of the stent, the graft, or the stent-graft. The covered prosthesis can be used to isolate cells, aneurysms, vessel wall defects, and the like. Suitable covering materials include bioabsorbable polymer (such as polylactic acid, poly(trimethylene carbonate) or PGA/TMC), fluoropolymer (such as fluorinated ethylene propylene or FEP, polytetrafluoroethylene or PTFE and expanded fluoropolymer, such as expanded polytetrafluoroethylene or ePTFE), fluoroelastomer (for example, TFE/PMVE copolymers), polyester (such as polyethylene terephthalate or PET), polyethylene, polypropylene, polyurethane, metal mesh (such as a woven or cut nitinol sheet) silicone, etc.

The covering material can form a lattice having a plurality of openings. In an embodiment, the covering lattice material having a plurality of openings is attached to one or more surfaces of a stent, graft, or stent graft. In such an embodiment, the covering lattice material can partially cover one or more surfaces of the stent, graft, or stent graft.

A lattice covering can have various uses. The lattice covering can be attached to one surface or multiple surfaces of a stent, graft, or stent graft. For example, a lattice covered stent can provide plaque stabilization and scaffolding, while simultaneously allowing perfusion of blood from the inner lumen of the stent if the openings are sized appropriately. This can be beneficial, for example, to perfuse side branch blood vessels. Alternatively, the relatively small lattice openings can be provided (for example about 40 or 50 µm) to relieve pressure from weakened portions of a blood vessel (for example, to treat a cerebral aneurysm). The relatively small lattice openings also can be useful for preventing encroachment of tissue from the patient into the inner lumen of the stent (for example, when the stent is placed near cancerous tissue), while still permitting side branch perfusion.

Figure 1B:
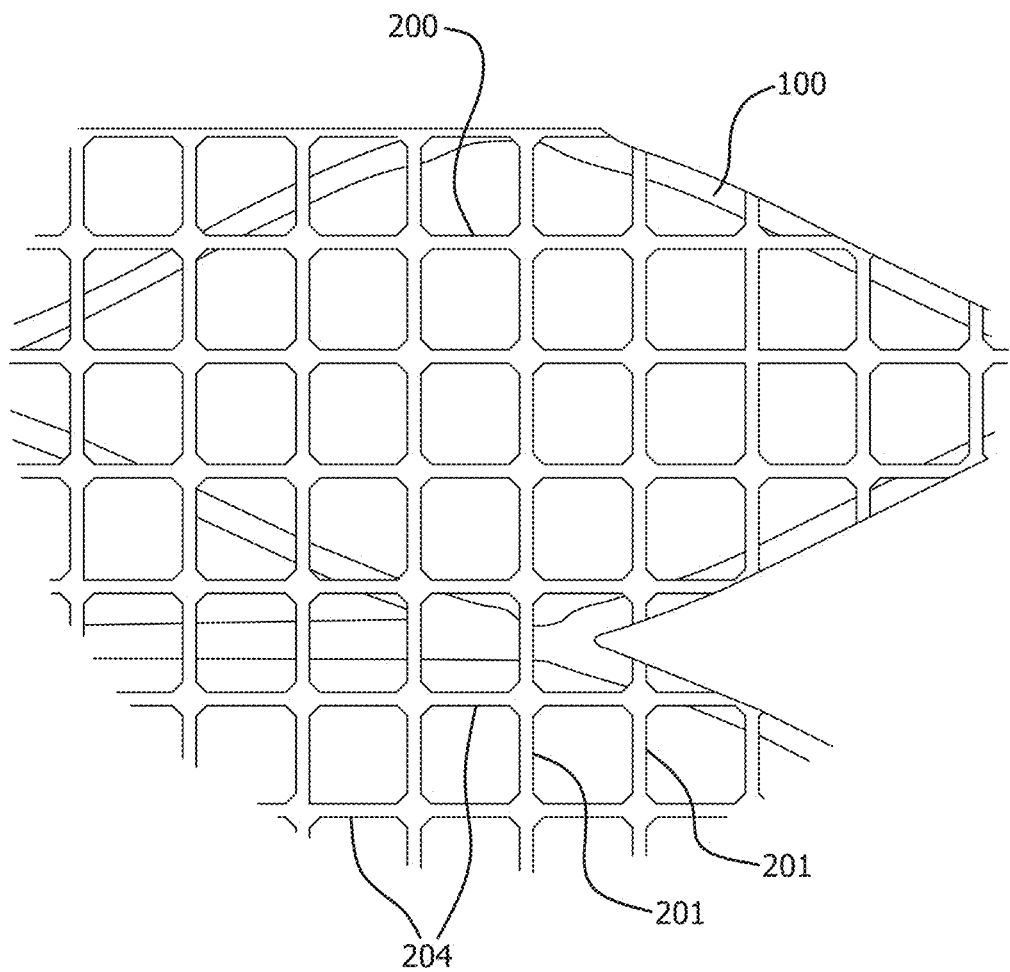
FIG. 1B is a close-up view of the stent illustrated in FIG. 1A.

FIGS. 1A and 1B illustrate two kinds of coverings, which can be termed to be lattices 200, which are attached to structures, which can be termed to be stents 100. These lattices are unitary structures. A series of interconnected, continuous segments define one or more patterns of openings in the lattice. The width of the lattice segments ranges between about 0.02 mm and about 0.2 mm, between about 0.02 mm and about 0.1 mm, or about 0.05 mm. The thickness of the lattice segments ranges between about 0.02 mm and about 0.2 mm, between about 0.02 mm and about 0.1 mm, or about 0.05 mm. The lattice opening size is the diameter of the largest inscribed circle, and ranges between about 40 µm and about 1 mm, between about 50 µm and about 800 µm, between about 100 µm and about 750 µm, or between about 200 µm and about 500 µm. The lattice opening size can be the size of the smallest kerf width of a laser. A lattice opening for use in an application such as aneurysm exclusion can be between about 10 µm and about 40 µm, between about 12 µm and about 30 µm, or between about 15 µm and about 20 µm.

Figure 1C:
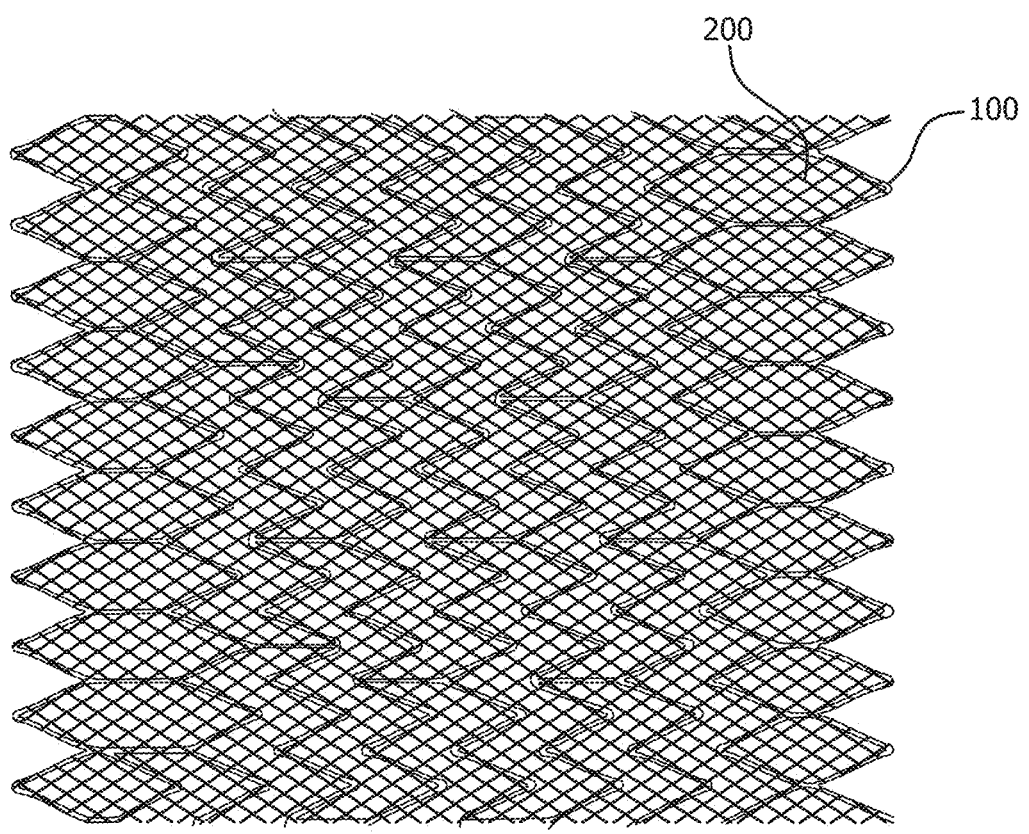
FIG. 1C is a plan view of a stent with a diamond-shaped lattice covering.

The lattice openings can be arranged in various regular and irregular patterns to provide diametrically stable functionality. The openings can have various shapes, such as triangles, squares, diamonds, parallelograms, hexagons, circles, or any other geometric shape, or combinations of shapes. FIGS. 1A and 1C show illustrative square and diamond-shaped openings, respectively.

The square-shaped lattice of FIGS. 1A and 1B have a series of continuous longitudinal segments (204) that extend in a direction that is substantially parallel to a longitudinal axis of the prosthesis, and a series of continuous circumferential segments (201) that extend in a direction that is at an angle approximately transverse to the longitudinal axis of the prosthesis. In FIG. 1B, the square-shaped openings have four equal or substantially equal sides and its interior angles are all at or approximately right angles (90°).

The arrangement of the square-shaped lattice of FIG. 1B can provide longitudinal segments with substantially constant length in an insertion or constrained configuration (when the prosthesis, such as a stent, has a reduced profile), and in a deployed configuration (when the prosthesis, such as a stent, has an enlarged profile greater than the insertion profile). For example, as compared with overall length of longitudinal lattice segments in the deployed configuration, the longitudinal segments of the lattice can have lengths ±5% in the insertion configuration, ±4% in the insertion configuration or ±2% in the insertion configuration.

Alternatively, the lattice covering can have parallelogram-shaped openings. Continuous longitudinal segments extend in a direction that is substantially parallel to the longitudinal axis of the prosthesis, such as a stent. Continuous circumferential segments extend at an angle with respect to the longitudinal axis that is greater than 0° and less than about 90° with respect to the longitudinal axis. For example, the circumferential segments can be oriented at an angle of about 45° with respect to the longitudinal axis. In an embodiment, a parallelogram-shaped lattice can be positioned with respect to a stent so that one or more of the longitudinal segments extend along the length of the closed cell connectors.

Further, the lattice covering can have diamond-shaped openings as shown in FIG. 1C. Two sets of continuous circumferential segments extend at different angles with respect to the longitudinal axis of the prosthesis. For example, a first set of the circumferential segments is oriented at an angle of about 45° with respect to the longitudinal axis, while a second set of the circumferential segments is oriented at an angle of about −45° and about −90° with respect to the longitudinal axis. In the lattice depicted in FIG. 1C, there are no longitudinal segments.

Yet still more lattice opening shapes can be obtained, such a triangles, or trapezoids, with additional lattice segments. For example, the lattice can have two sets of circumferential segments, as well as longitudinal segments. One set of the circumferential segments can be oriented at an angle of between about 45° and about 90° with respect to the longitudinal axis, while a second set of the circumferential segments can be oriented at an angle of between about −45° and about −90° with respect to the longitudinal axis.

When the lattice is provided as a covering for a stent, longitudinal and/or circumferential lattice segments can be positioned to extend along one or more stent struts. For example, in FIG. 2B, longitudinal segments of the square-shaped openings extend along one of the closed cell connectors of the circumferential member, and are longitudinally aligned with it. The number of longitudinal segments of the lattice covering can be the same as or greater than the number of the closed cell connectors in each of the circumferential members. One, some, or all of the longitudinal members can be joined with the closed cell connectors. Similarly, other shaped openings of the lattice can be aligned so that one or more sides extend along the length of one or more connector struts within the stent.

Figure 2A:
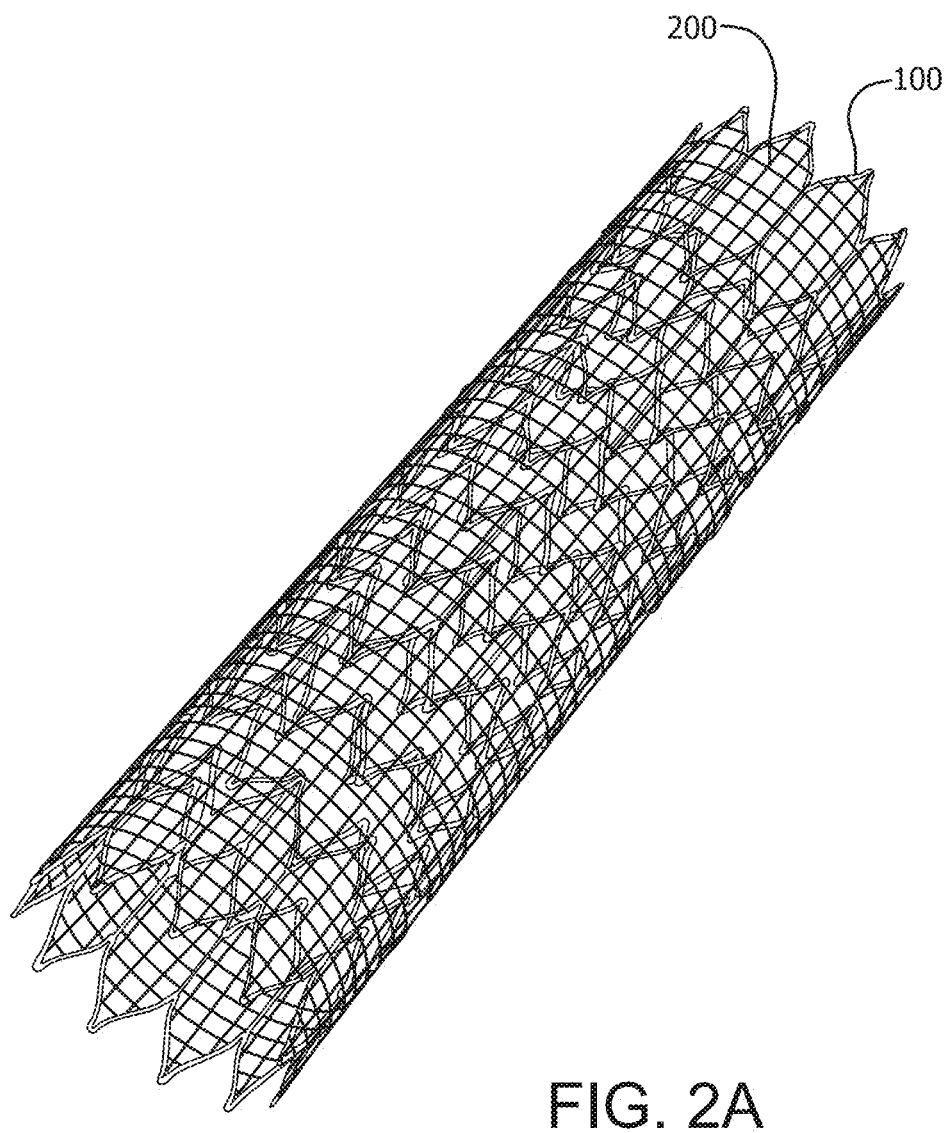
FIG. 2A is a full view of a stent with a square-shaped lattice covering.
Figure 2B:
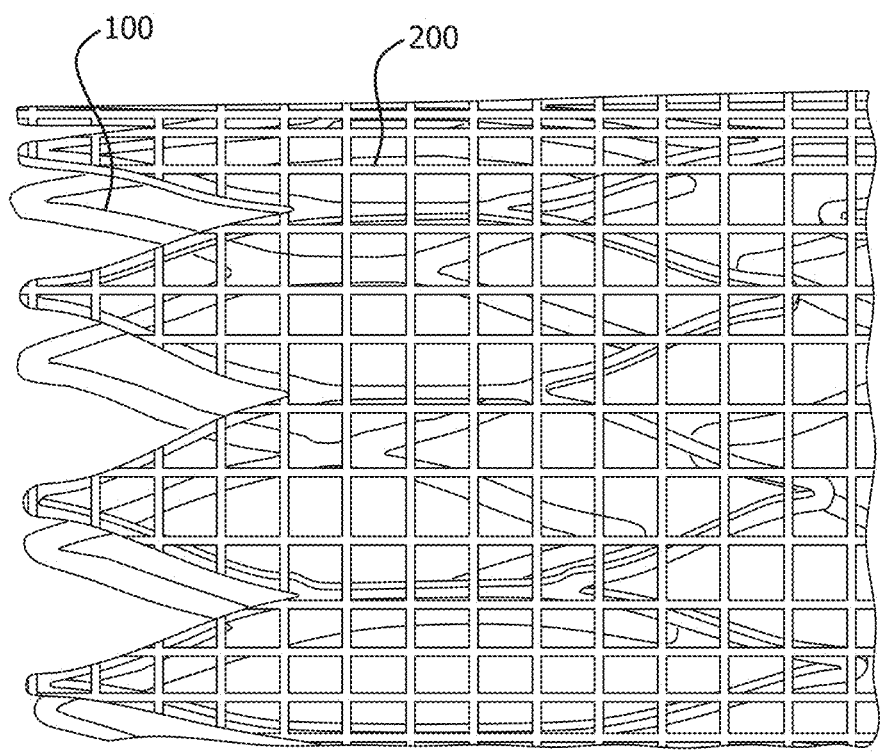
FIG. 2B is a close-up view of a stent at one of its ends with a square shape lattice.
Figure 2C:
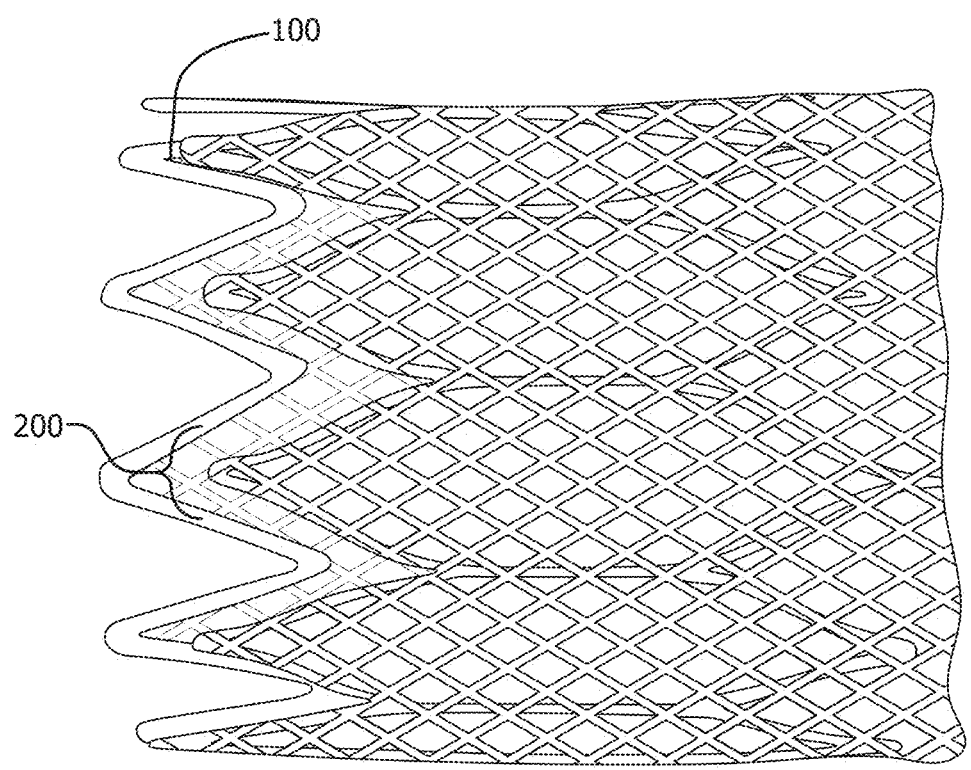
FIG. 2C is a close-up view of a stent at one of its ends with a diamond shape lattice.

The number of attachments between a stent and the lattice covering can be varied depending on various factors, such as the size of the stent openings, the size of the lattice openings, and the orientation of the lattice with respect to the stent. In FIGS. 2B and 2C, the closed cells of the stent have a larger dimension along the longitudinal axis, and a shorter dimension transverse to the longitudinal axis. In FIG. 2B, the square-shaped lattice covering is oriented with fewer lattice openings across the larger dimension of the closed cell, and an equal or fewer lattice openings across the smaller dimension of the closed cell. In FIG. 2C, the diamond-shaped lattice covering is oriented with more lattice openings across the smaller dimension of the closed cell than in FIG. 2B.

A substantially uniform lattice opening pattern is shown in FIGS. 1A-1C. In those lattices, the size and shape of the openings is substantially uniform throughout. However, the lattice opening pattern also can be irregular. Lattice openings can be provided in one portion and not in the balance of the lattice. For example, a first arc of the lattice can have openings along the entire length of the lattice while a second arc opposite of the first arc is substantially without openings. Alternatively, the lattice openings can be provided in along a spiral with respect to the longitudinal axis. Further still, the lattice can have a perfusion region within which the openings are provided and an excluding region devoid of openings, thus, configured to allow orientation of the perfusion region to be determined endovascularly.

Alternatively, the lattice openings can have several patterns. The openings of similar size and shape can be grouped together to have at least two sets of openings with each set having a predetermined size and shape, or uniformly distributed throughout the lattice. For example, lattice openings corresponding to the circumferential members can be square-shaped as depicted in FIG. 1A, while the lattice openings corresponding to the helical element can be diamond-shaped as depicted in FIG. 1C.

Alternatively, the lattice can have three sets of openings distributed along the length of the lattice, one at the proximal end, one at the distal end and one in-between. The openings of the proximal set, for example, can have diamond-shaped openings with a nominal diameter of about 300 μm as measured by the largest inscribed circle. The openings of the distal set, for example, can also have diamond-shaped openings but with a nominal diameter of about 500 μm as measured by the largest inscribed circle. On the other hand, the openings of the central set, those that span between the proximal and distal sets, can have squared-shaped openings with a nominal diameter of about 100 μm as measured by the largest inscribed circle. Other permutations, sets, and groupings are also envisioned. For example, in addition to the square or diamond-shaped lattice openings, one or more large oval openings adapted to allow for side branch perfusion can be provided.

The lattice can be produced by laser cutting, such as a $CO_2$ laser, from a longitudinally wrapped tube of, for example, six layers of biaxially-oriented film made from one suitable covering material or from a combination of suitable covering materials to produce a unitary structure, not woven. Such a lattice could have a nominal thickness between about 10 μm and about 250 μm, between about 20 μm and about 60 μm, or between about 35 μm and about 50 μm. Other films can be used together with the biaxially-oriented films or in place of them to form the lattice. For example, uniaxially-oriented or multiaxially-oriented films can be used. These films can be wrapped longitudinally as described above, or can be wrapped in other configurations. For example, the films can be helically wound to form the tubular structure. Other methods of lattice preparation are also envisioned in accordance with the procedures described in U.S. Pat. Pub. No. 2008/0119943 to Armstrong et al., or U.S. Pat. No. 7,306,729 to Bacino et al., the entire disclosures of which are incorporated herein by reference. Alternatively, a lattice can also be formed from a fiber by techniques such a knitting, weaving, or crocheting.

Conformability of the stent with and without the lattice can be measured according various known test methods. For example, ISO 25539-2 (2008) describes one protocol for assessing the ability of medical devices to conform to vessel walls and is incorporated in and constitutes a part of this specification. Most generally, the test method measures the smallest radius of curvature that a stent can withstand without kinking. A more conformable stent will have greater ability to conform to bends having a smaller radius of curvature without kinking, and a less conformable stent will have a lesser ability to conform to such bends without kinking.

Flexibility of the stent with and without the lattice can be assessed by a three-point bend test on deployed stents. One method for such testing is set forth in ASTM F2606-08, the entire disclosure of which is incorporated herein by reference. Most generally, after the stent is placed into a specific three-point bend fixture, the amount of force required to bend the stent is measured. The resulting load-deflection curves can be used to assess flexibility of stents. A more flexible stent will have greater ability to bend at lower forces, and a less flexible stent will have a lesser ability to bend at lower forces.

The stent, stent graft, and/or vascular graft and the lattice can be sized to be the same or different. For instance, the lattice covering a stent as shown in FIGS. 1A, 1C, 2A and 2B does not notably constrain the stent. For example, the stent has an outer diameter of about 8 mm, and the lattice has an inner diameter of about 8 mm.

Alternatively, however, the lattice can resist full expansion of the stent, e.g. a self-expanding stent, depending upon lattice geometry and material chosen. This can be achieved by over-sizing the stent with respect to the lattice covering. The stent can have an outer diameter that is oversized with respect to the lattice covering in an amount of about 10% to about 100%, between about 20% and about 70%, or between 30% and about 50%. For example, the self-expanding stent can have an outer diameter of about 10 mm, and the lattice can have an inner diameter of about 8 mm. An effect of oversizing the stent as compared to the lattice (in this example to about 20%) is to provide a final self-expanding device that resists forces tending to collapse the deployed stent. The amount of force needed to reduce the diameter of the deployed stent is higher when an oversized self-expanding stent is used as compared with the same stent that is not oversized.

In addition to oversizing the stent as compared with the lattice, the lattice can be made from a rapidly recovering distensible material that is capable of being stretched and then recovering. A rapidly recovering distensible material for the lattice can be made according to various known techniques, such as in accordance with the procedures described in U.S. Pat. Nos. 4,877,661 and 5,026,513 to House et al., the entire disclosures of which are incorporated herein by reference. The lattice made from rapidly recovering distensible material can have a rapid recovery of greater than about 5.5%, greater than about 15%, or greater than about 30%. For example, the stent can be sized to have an outer diameter of about 8 mm, and the rapidly recovering distensible lattice can be sized to have an inner diameter of about 6 mm. Although the above embodiments describes a stent and lattice, other prosthesis can be used in combination with a lattice, including, but not limited to stent-graft and vascular grafts The lattice can have longitudinal and/or circumferential lattice segments of varying length that are configured to provide resistance to dilation and creep and expand in a sloped or a stepped manner. The terms "dilation" and "creep" as used herein are meant to denote chronic time-dependent radial or longitudinal expansion of the prosthesis in response to physiological or stent-induced stress on the prosthesis. The segments in the lattice can be configured to plastically deform or rupture depending on the prescribed diametrical dimension and the applied pressure. The lattice covering 200 shown in FIG. 5A is not constrained and expands radially into an enlarged first diametrical dimension d1. A circumferential segment 201 of the lattice 200 is under load and resistant to further expansion, whereas circumferential segments 202 and 203 are tension-free. The circumferential segment 202 is constructed with excess length (shown as a hump) that allows the circumferential segment 202 to expand to an enlarged second diametrical dimension d2. The circumferential segment 203 is also constructed with excess length (shown as two humps) that allows the circumferential segment 203 to expand to an enlarged third diametrical dimension d3. The lattice 200 can be adjusted to a further enlarged second diametrical dimension d2 as shown in FIG. 5B, when distensive force is applied to the lattice 200. When the distensive force reaches a prescribed pressure, the circumferential segment 201 ruptures. Alternatively, instead of rupturing, the circumferential segment 201 can be plastically deformed. A balloon catheter can be used to exert the distensive force. Once the lattice 200 expands radially into an enlarged second diametrical dimension d2, the circumferential segment 202 assumes the load. However, the circumferential segment 202 is resistant to further expansion, whereas circumferential segment 203 is still relaxed. The lattice 200 can be adjusted to a further enlarged third diametrical dimension d3 as shown in FIG. 5C, when distensive force is applied to the lattice 200. When the distensive force reaches a prescribed pressure, the circumferential segment 202 ruptures and the circumferential segment 203 assumes the load. Alternatively, the circumferential segment 201 can be plastically deformed instead of rupturing. Although, only three segments of varying length are shown in FIGS. 5A-5C, the number can range from 2 to 1000. The width of the segments can also vary depending on the pressure at which the segments are desired to be plastically deformed or ruptured.

Figure 8A:
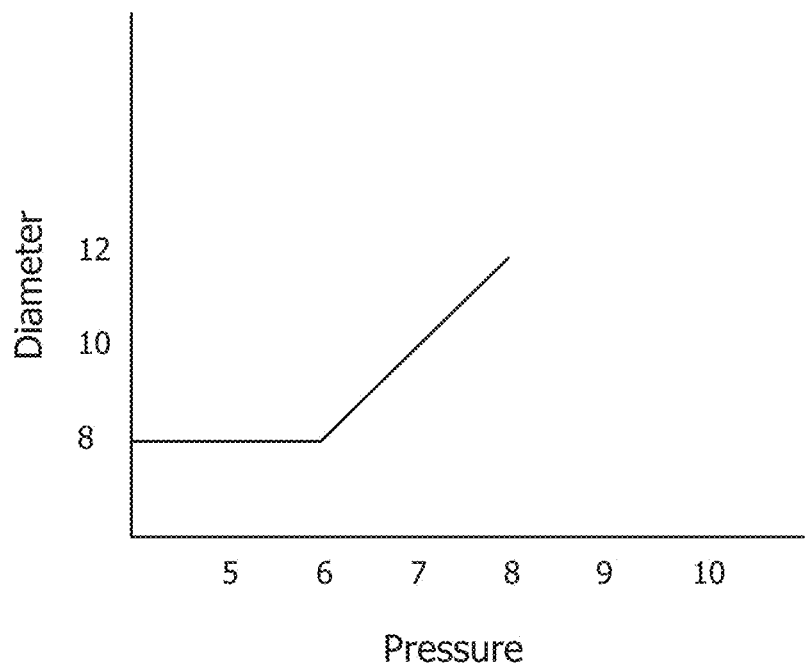
FIG. 8A is a plot of a diameter of the lattice that is configured to expand in a sloped manner as a function of the distensive pressure.
Figure 8B:
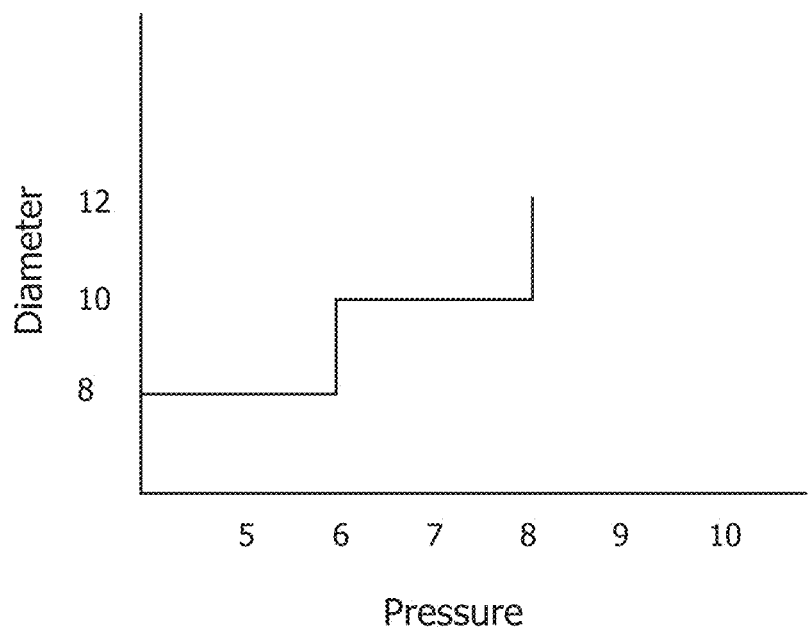
FIG. 8B is a plot of a diameter of the lattice that is configured to expand in a stepped manner as a function of the distensive pressure.

FIGS. 8A and 8B show a relationship between the pressure applied during expansion and the diameter of the lattice. As depicted in FIG. 8A, if the segments are plastically deformed, the lattice expands in a sloped manner. For example, a lattice can have a diameter of 8 mm and it holds such diameter until the pressure reaches about 6 atm. Once 6 atm is exceeded, the lattice begins to plastically deform. Continued application of pressure results in continued diametrical increase until the lattice ruptures or, as shown in FIG. 8A, it reaches a "hard-stop" built into the lattice, e.g., diameter of 12 mm. As depicted in FIG. 8B, if the segment ruptures, the lattice expands in a stepped manner, thus allowing for discreet diametrical steps. For example, a lattice can have a diameter of 8 mm and it holds such a diameter until the pressure reaches about 6 atm. Once 6 atm is exceeded, certain segments that are resistant to further expansion break and the lattice instantly expands to a diameter of about 10 mm. Again, the lattice holds such a diameter until the pressure reaches about 8 atm. Once 8 atm is exceeded, certain segments that are resistant to further expansion break and the lattice instantly expands to a diameter of about 12 mm.

Figure 13:
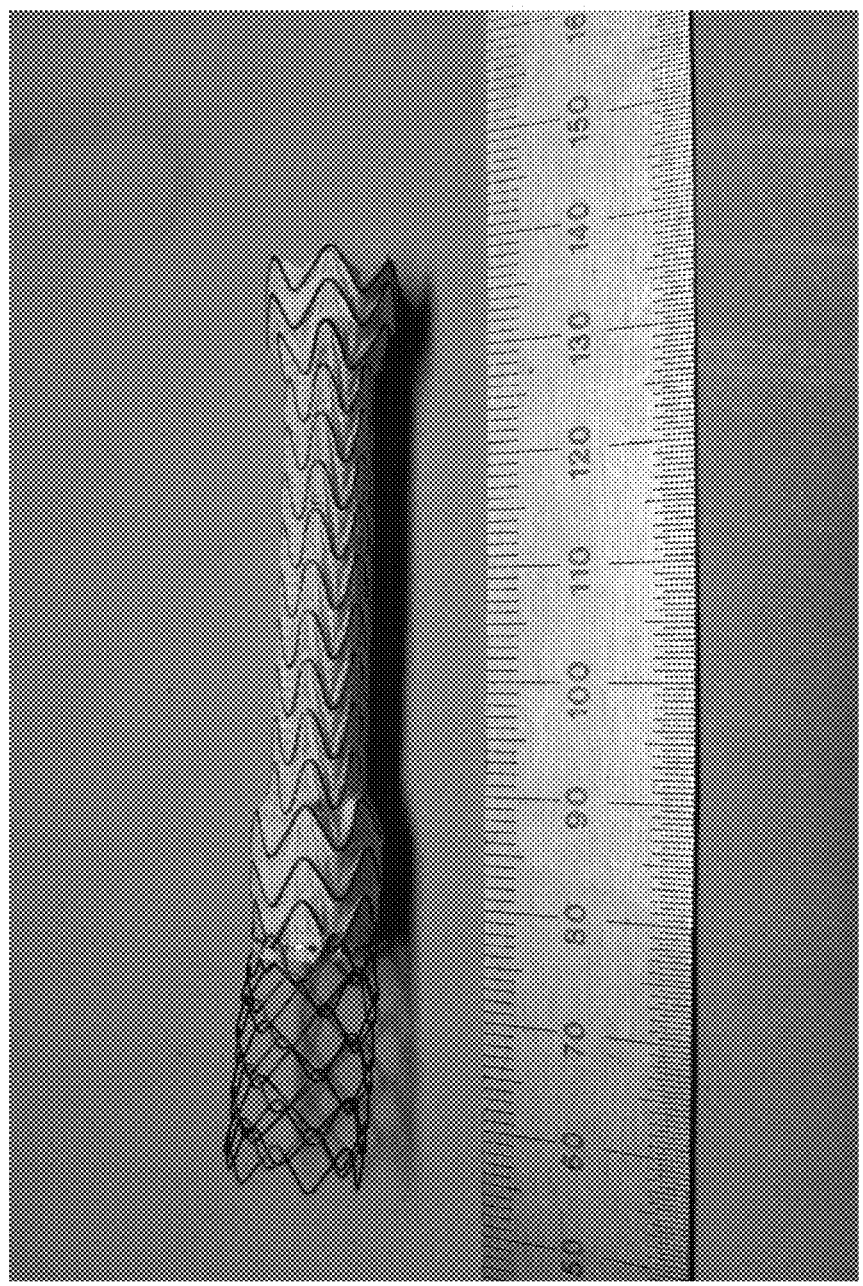
FIG. 13 is a prosthesis having a constrained mid-section by a lattice structure.

In addition to expanding the whole prosthesis, only a portion can be radially or longitudinally expended that can provide a high degree of accuracy during implementation. Any portion of the prosthesis can be expanded to create any shape, such as a dog bone shape, an hour glass shape, or a taper. For example, the proximal and distal ends of the prosthesis can be expanded to retain a dog bone shape shown in FIG. 13 that is resistant to dilation and creep. The prosthesis can be tapered along all or a portion of its length so that the diameter changes along the length. A tapered length section may be located closer to either end of the prosthesis, or the taper may exist as a uniform, gradual taper extending between the prosthesis ends.

Figure 6A:
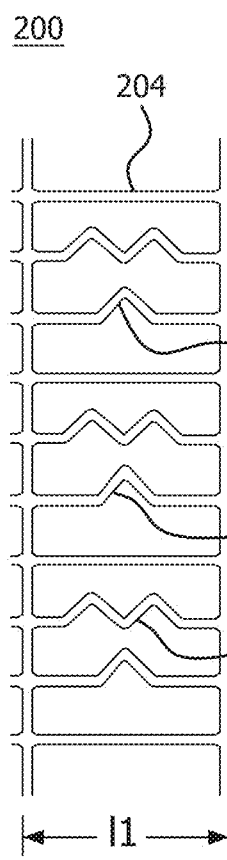
FIGS. 6A-6C illustrate a partial close-up of a lattice with longitudinal segments of varying length during longitudinal expansion.
Figure 6B:
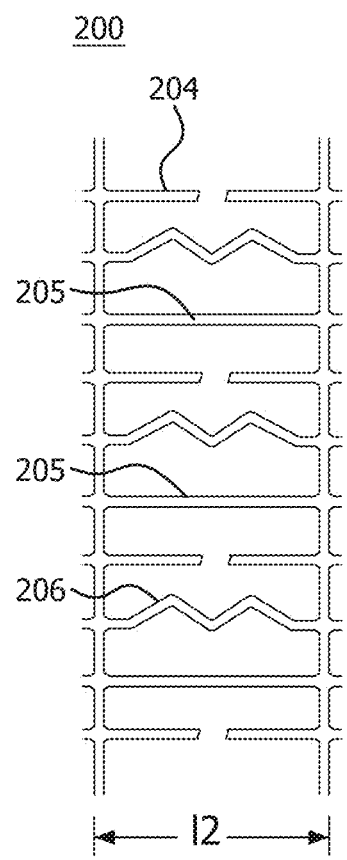
Figure 6C:
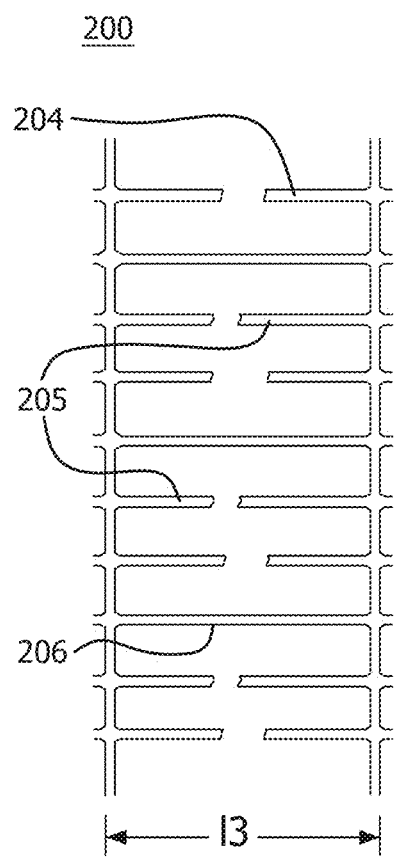

A lattice covering can allow an adjustment in its length. The lattice 200 shown in FIG. 6A has longitudinal segments of varying length that are substantially parallel to a longitudinal axis of the prosthesis. The lattice 200 shown in FIG. 6A is not constrained and expands longitudinally into an enlarged first linear dimension 11. A longitudinal segment 204 of the lattice 200 is under load and resistant to further expansion, whereas longitudinal segments 205 and 206 are not under load. The lattice 200 can be adjusted to a further enlarged second linear dimension 12 as shown in FIG. 6B, when a force is applied to the lattice 200. When the force reaches a prescribed pressure, the longitudinal segment 204 ruptures and the lattice 200 expands to a further enlarged second linear dimension 12. Alternatively, instead of rupturing, the longitudinal segment 204 can be plastically deformed. The process can be once again repeated as the linear expansion continues into the third enlarged linear dimension 13 shown in FIG. 6C.

Figure 11A:
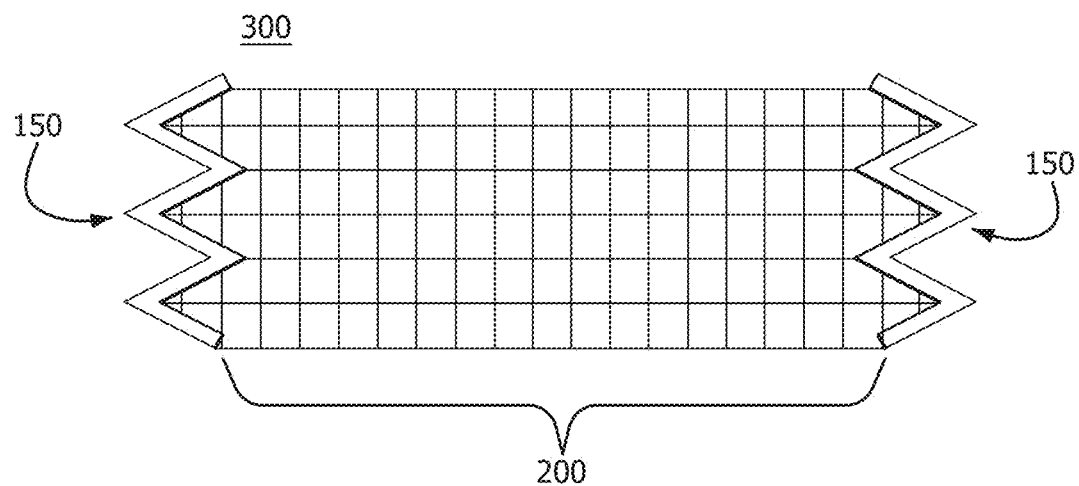
FIG. 11A is an accessory lattice.
Figure 11B:
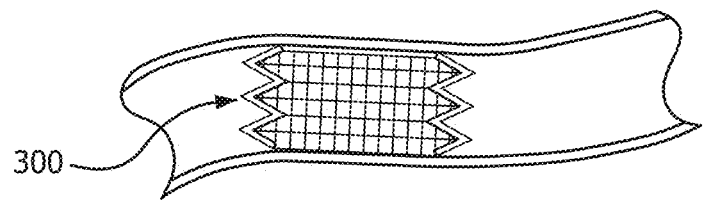
FIGS. 11B-11D illustrate the deployment steps of an accessory lattice.
Figure 11C:
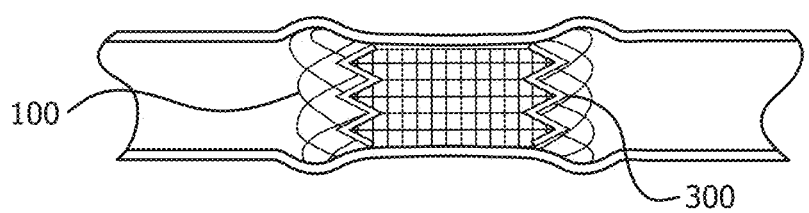
Figure 11D:
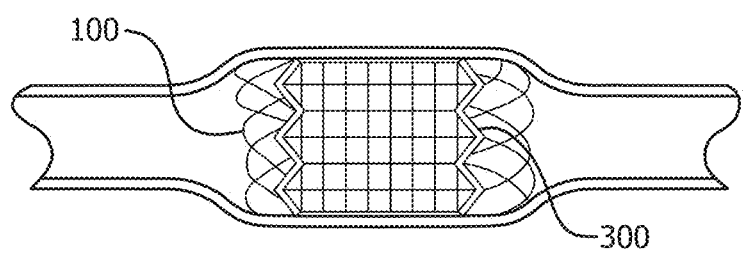

In addition to providing the lattice that can have lattice segments of varying length configured to expand in a sloped or a stepped manner, the lattice can also have a stent or stent frame attached at either end of the lattice, or the lattice can be interposed between two stents or stent frames. By incorporating the lattice between two stent frames, such device can function as an "accessory" prosthesis that can constrain the primary prosthesis deployed within it, yet allow diametrical adjustment as deemed necessary. Herein, the term "primary prosthesis" is defined as the main device chosen as therapy for the treatment site. An accessory prosthesis 300 is shown in FIG. 11A. The prosthesis 300 has a lattice 200 interposed between two stent frames 150 at its distal and proximal ends. The accessory prosthesis can be deployed in a prescribed lumen prior to the deployment of the primary prosthesis as depicted in FIG. 11B. A delivery system of such a device may be by means of mechanical or hydraulic distension or a sheath-type delivery system if the device is configured to self-expand. Deployment of the accessory prosthesis can be immediately prior to the deployment of the primary prosthesis or as a staged procedure. In the staged procedure, the accessory stent can be deployed one day, two days, one week, two weeks or any other prescribed time before the deployment of the primary prosthesis. If deployed immediately prior to the deployment of the primary prosthesis, both the accessory prosthesis and the primary prosthesis can be provided on the same catheter, yet spaced axially apart. Once the accessory prosthesis lattice device is deployed, the catheter system can then be advanced and the primary prosthesis deployed within it. Such a setup can reduce procedural time and radiation exposure by eliminating catheter exchanges while also minimizing introductory profile. As shown in FIG. 11C, a stent 100 is deployed within the accessory prosthesis 300. If necessary, the accessory prosthesis 300 can be radially expanded with the stent 100 as shown in FIG. 11D. The open structure of lattice 200 allows intended host biological response and interaction with the abluminal surface of the primary prosthesis. For instance, if the abluminal surface of the primary prosthesis is coated with a drug or has an engineered microstructure to accelerate cellular ingrowth, the lattice will minimally inhibit these functions.

Figure 3C:
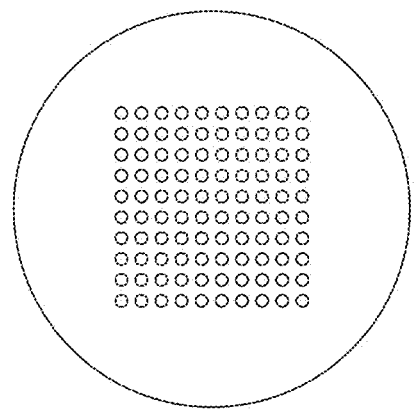
FIG. 3C is a partial close-up view of a lattice after a micro-catheter is advanced through a lattice opening.
Figure 3B:
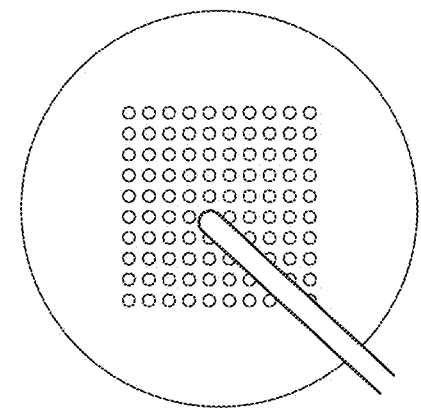
FIG. 3B is a partial close-up view of a lattice as a micro-catheter is advanced through a lattice opening.
Figure 3A:
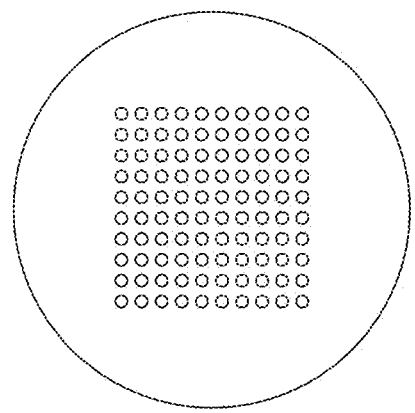
FIG. 3A is a partial close-up view of a lattice prior to a micro-catheter advancing through a lattice opening.

A lattice covering can stretch or deform when advancing a catheter or other tool from a deployment system through its sidewall to allow crossing for deployment of a side branch device or other device. The lattice can substantially return to its structure, size and shape once the side branch or additional device is deployed and that deployment system removed from the lattice. FIG. 3A is a partial view of a lattice covering prior to micro-catheter advancement. FIG. 3B is a partial view of the lattice with a micro-catheter advancing through one of the lattice openings and showing the opening deforming to take the shape of the outer diameter of the micro-catheter. FIG. 3C is a partial view of the same lattice in FIG. 3B after the micro-catheter is removed and shows that the lattice opening has substantially returned to its original size and shape. In another method, a balloon catheter is advanced through one of the lattice openings instead of a micro-catheter. The balloon is deployed to size the opening for placement of a side branch stent, graft or stent graft. In sizing, the lattice opening can deform to take the shape of the outer diameter of the balloon. Once the side branch stent, graft or stent graft is placed into the balloon sized opening of the lattice, the lattice opening conforms to the shape of the side branch stent, graft or stent graft.

A lattice covering can be formed from longitudinal strips of any of the covering materials described herein including by bonding or weaving into a basket weave, mesh, or lattice pattern that define a plurality of openings.

Figure 4C:
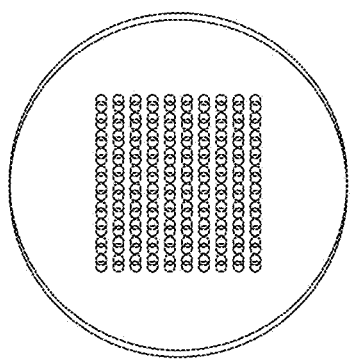
FIG. 4C is a partial close-up of the lattice of FIG. 4B applied to the lattice of 4A.
Figure 4B:
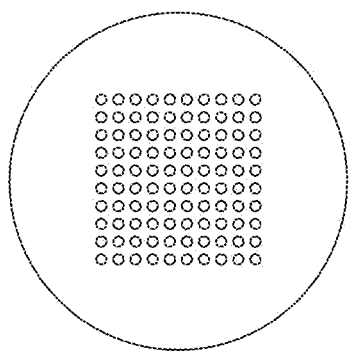
FIG. 4B is a partial close-up of a lattice.
Figure 4D:
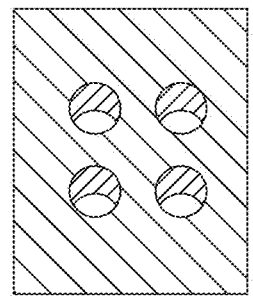
FIG. 4D is a partial close-up of the lattice openings in the lattice of FIG. 4C.
Figure 4A:
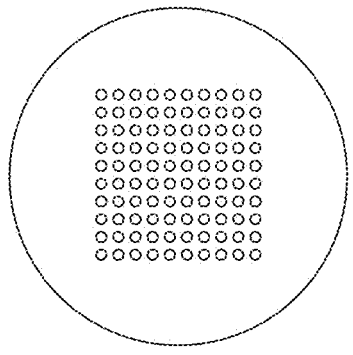
FIG. 4A is a partial close-up of a lattice.

Optionally, a stent, graft, or stent-graft can be covered with multiple layers of coverings. A lattice can be formed by two or more layers of lattice coverings. Two or more layers can be bonded together with openings aligned or offset. One or more of the layers can have elastic properties. As used herein, the term "elastic" refers to the property of a material to be elongated upon the application of a force and that returns to its approximate original dimensions upon the release of the force due to the retraction force of the material. Two lattice coverings as shown in FIGS. 4A and 4B can be layered such that the openings are offset or staggered as shown in FIG. 4C. The resulting open area, as shown in FIG. 4D, may provide smaller trans-mural porosity than may be achieved by utilizing a single lattice covering.

One or more of the layers within a lattice can have same or different expanded diameter. The lattice having multiple layers with different expanded diameters can be configured to expand in a stepped rather than sloped manner while providing resistance to dilation and creep. A least one layer in such a lattice has a fully expanded diametrical dimension diameter that is greater than at least one other layer in the same lattice. When not constrained the lattice can expand radially into an enlarged diametrical dimension that is lesser of two. At this level of expansion, at least one layer is under tension and is resistant to further expansion. The lattice, however, can be adjusted to a further enlarged second diametrical dimension when distensive force is applied to the lattice and at a prescribed pressure, the layer that is resistant to further expansion fails. For example, the linking segments within the layer are plastically deformed or ruptured. Once the lattice expands radially into an enlarged second diametrical dimension, at least one other layer assumes the load and is resistant to further expansion.

As depicted in FIGS. 7A-7D, the lattice 200 has three layers 200a, 200b, and 200c. Each layer has at least two longitudinal segments (204, 205, 206) and at least two circumferential segments (201, 202, and 203). Each circumferential segment 201 of layer 200a has a fully expanded dimension x. Each circumferential segment 202 of layer 200b is built at dimension x but has a fully expanded dimension y. Each circumferential segment 203 of layer 200c is built at dimension x but has a fully expanded dimension z. The relationship between the illustrated dimensions is z>y>x. When not constrained the lattice 200 can expand radially into an enlarged diametrical dimension x. At this level of expansion, layer 200a is under tension and is resistant to further expansion. The lattice 200 can be adjusted to a further enlarged second diametrical dimension y when distensive force is applied to the lattice 200. When the prescribed pressure is exceeded, layer 200a of the lattice 200 fails, i.e., ruptures or plastically deforms. For example, the circumferential segments 201 within layer 200a are plastically deformed or ruptured. The lattice 200 expands radially into an enlarged second diametrical dimension y. Layer 200b of the lattice 200 assumes the load and is resistant to further expansion. Once again, the lattice 200 can be adjusted to a further enlarged third diametrical dimension z when distensive force is applied to the lattice. When the prescribed pressure is exceeded, layer 200b of the lattice 200 fails. Lattice 200 expands radially into an enlarged third diametrical dimension z. Once the lattice 200 expands radially into an enlarged third diametrical dimension z, layer 200c of the lattice 200 assumes the load and is resistant to further expansion.

Figure 7A:
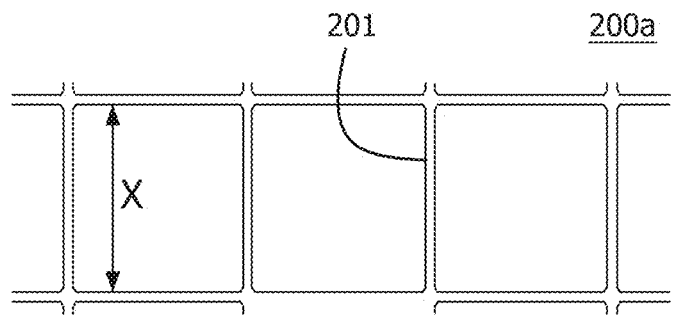
FIGS. 7A-7C illustrate a partial close-up of each layer within a multi-layer lattice.
Figure 7B:
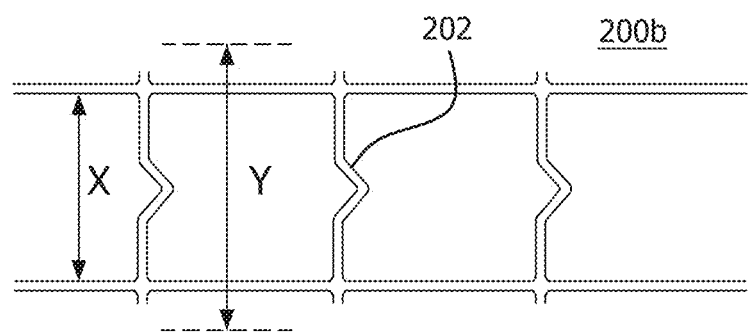
Figure 7C:
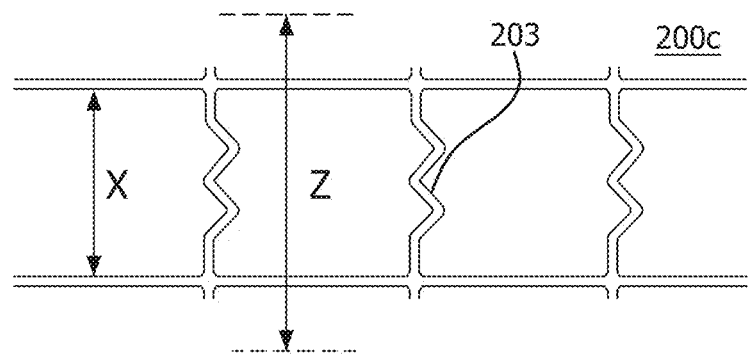
Figure 7D:
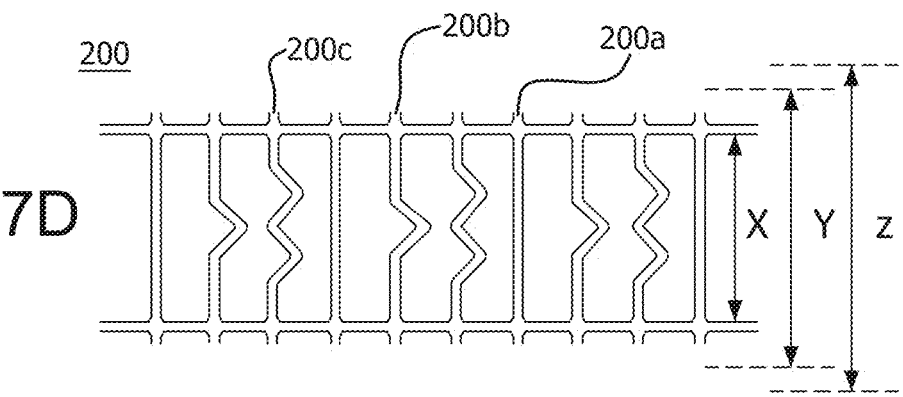
FIG. 7D is a partial close-up of a multi-layer lattice.

Alternatively, the multi-layer lattice can be configured to radially and/or longitudinally expand in a partially stepped and a partially sloped manner. With reference to FIG. 7D, for example, the segments in layer 200a are broken, the segments in layer 200b are plastically deformed and the segments in layer 200c are broken.

Figure 12:
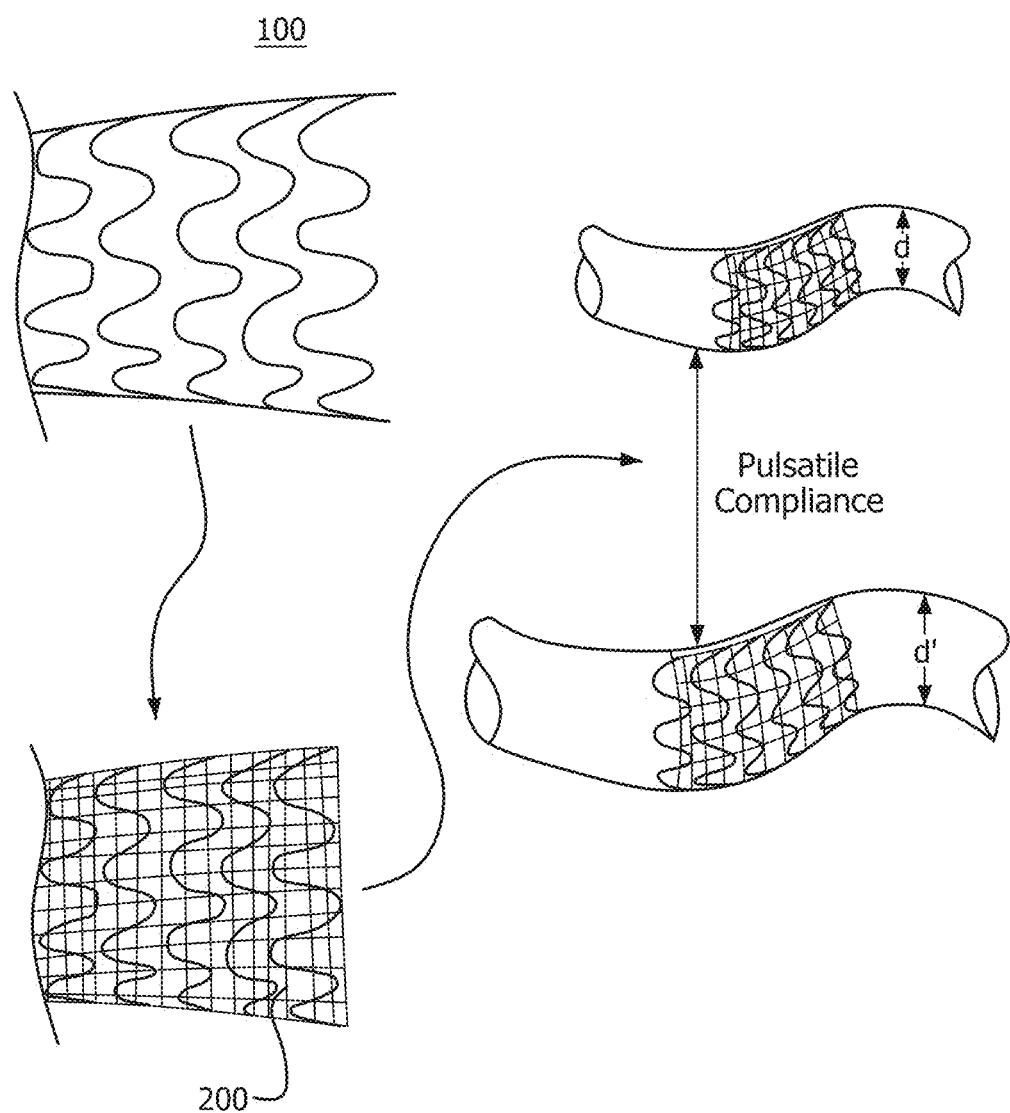
FIG. 12 illustrate the preparation and deployment of a prosthesis with pulsatile compliance.

The prosthesis is provided that is configured to have pulsatile compliance. The characteristic of pulsatile expansion and contraction of vessels requires fine mechanical compliance of the prosthesis, i.e., a close mimicking by the prosthetic device of the mechanics and timing of the natural vessel distending and reshaping under change in blood pressure. Such prosthesis has a stent. The stent can be flared at one or more ends. For example, both ends of the stent can be flared. That is, a diameter at an end of the stent is greater than a diameter defined at the center of the stent. The prosthesis further has a lattice defining a plurality of openings. These two components of the prosthesis have large differences in mechanical properties. The lattice is very flexible or elastic, and the stent is typically is very stiff in comparison. Thus, the combination produces a non-linear elastic response within the physiological pressure range of a natural vessel. The lattice can be made from a rapidly recovering distensible material and/or a material with elastic properties, for example a composite material, including at least one fluoropolymer membrane and elastomer. FIG. 12 illustrates the combination of a stent 100 with at least one end flared combined with a lattice 200, which can be deployed in a vessel to produce a non-linear elastic response to physiological pressure between diameters d and d'.

A lattice can be imbibed with PVA (polyvinyl alcohol) or other materials (e.g., gold, platinum/iridium, or the like) to aid the physician during imaging (e.g., ultrasound, fluoroscopy, MRI, or the like). A lattice can be imbibed with one or more therapeutic agents. The term "imbibed or imbibing" as used herein is meant to describe any means for at least partially filling a portion of the pores of a porous material such as ePTFE or the like. This can be done during manufacturing by, for example imbibing, or it can be done during catheter flushing which may imbibe or coat one or more therapeutic agents into or onto the lattice. Imbibing or coating of a therapeutic agent can result in release of the agent over time. One skilled in the art can select suitable therapeutic agents including without limitation: sirolimus, dexamethoasone, paclitaxel, phosphorylcholine, everolimus, or like agents. As used herein, a therapeutic agent can be a drug or other pharmaceutical product such as a non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, paclitaxel, etc. Where an agent includes a genetic therapeutic agent, such a genetic agent may include but is not limited to: DNA, RNA and their respective derivatives and/or components: hedgehog proteins, etc. Where a therapeutic agent includes a cellular material, the cellular material may include but is not limited to: cells of human origin and/or non-human origin as well as their respective components and/or derivatives thereof. Where the therapeutic agent includes a polymer agent, the polymer agent may be a poly-styrene-polyisobutylene-poly-styrene triblock copolymer (SIBS), polyethylene oxide, silicone rubber and/or any other suitable substrate. In at least one embodiment the polymer agent can be biodegradable such as PLA, PLGA, etc. A therapeutic agent can also be a coating material as described herein.

Figure 9A:
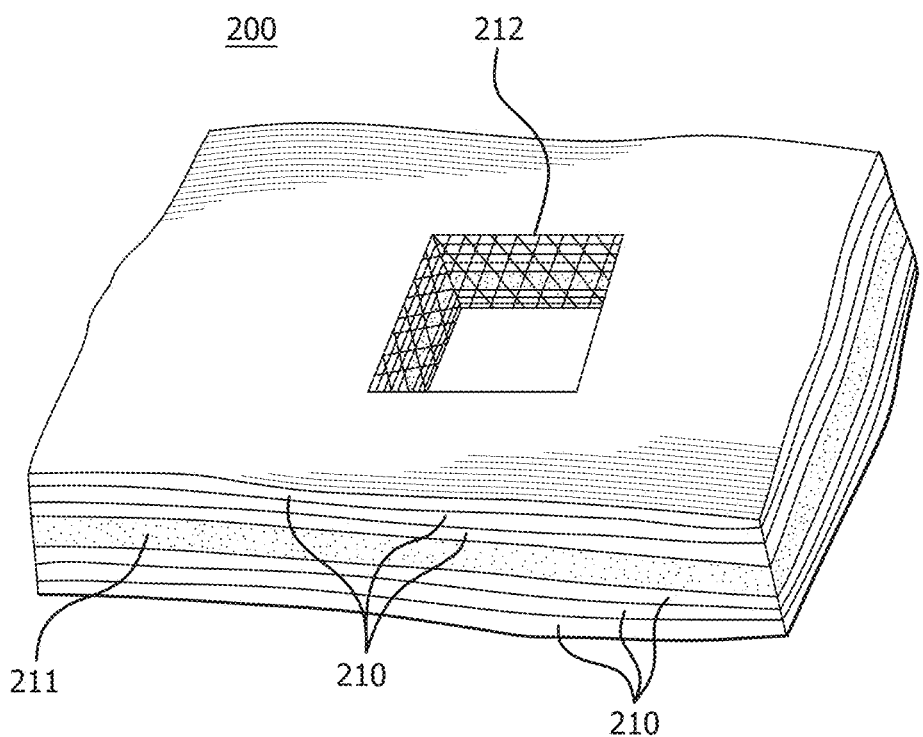
FIG. 9A is a partial close-up of a drug-eluting lattice.
Figure 9B:
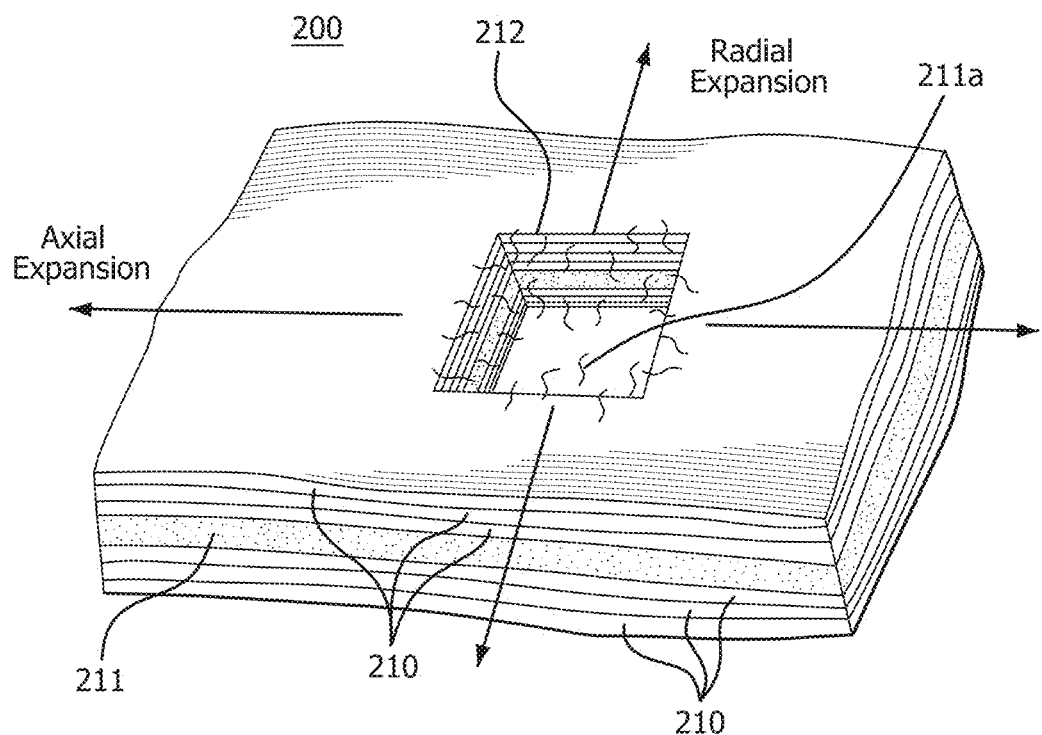
FIG. 9B is a partial close-up of a drug-eluting lattice during radial/longitudinal expansion.
Figure 10:
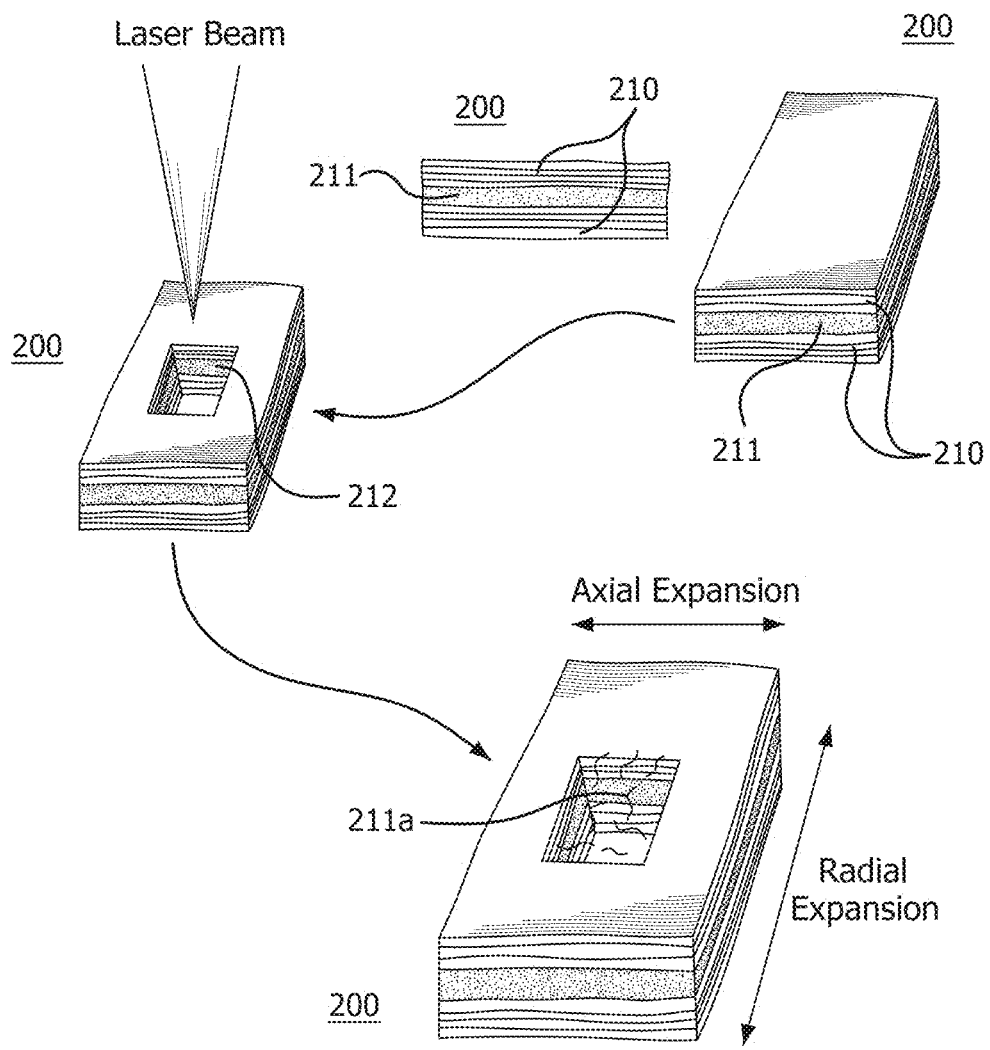
FIG. 10 illustrate preparation and deployment steps of a drug-eluting lattice.

A lattice can be imbibed with one or more therapeutic agents that can be released during distension. As shown in FIGS. 9A and 10, this can be done during manufacturing by preparing a multi-layer lattice 200 with a reservoir layer 211 having a therapeutic agent. The reservoir layer 211 is disposed between at least two layers 210, such as ePTFE, that are nonpermeable to the therapeutic agent. The openings 212 in the lattice can be produced by laser cutting, such as a $CO_2$ laser. During laser cutting, the polymer adhesive used in manufacture of a multi-layer lattice, such as FEP or TFE/PMVE, reflows and seals the inner walls of the openings 212, holding the therapeutic agent within the reservoir layer 211. To avoid any negative thermal effect on the therapeutic agent during manufacturing, the laser used for cutting openings in the lattice is substantially focused and the layers can be joined together by compression and the polymer adhesive reflow at the inner walls of the openings 212. As the prosthesis expands during deployment by means of mechanical or hydraulic distension, the nonpermeable layers 210 expand, for instance, radially into an enlarged diametrical dimension. Even in expanded state, the nonpermeable layers 210 typically do not allow the release of the therapeutic agent. In contrast, the inner walls of the openings 212 are compromised immediately upon expansion. As shown in FIGS. 9B and 10, the inner walls fail, break, crack or tear to allow the therapeutic agent 211a to be released. The cracks in the inner walls typically develop across the entire lattice that helps to achieve a high rate of release throughout the lattice by providing a conduit through which the therapeutic agent can easily and quickly diffuse from the reservoir layer.

A lattice can also be imbibed with an alginate. The alginate can be imbibed throughout the lattice or selectively to one or more portions of the lattice. The alginate can be cross-linked by delivering divalent or trivalent cations (for example, calcium) though a catheter or the prosthesis delivery system to the prosthesis delivery site. The cross-linked alginate portion of the lattice can be used to relieve pressure from weakened portions of a blood vessel (for example, to treat a cerebral aneurysm) or to occlude other openings or vessels adjacent to the sidewall of the stent. A lattice can be imbibed with calcium. An alginate can be delivered to the calcium imbibed lattice through the prosthesis delivery system or by another catheter system to cause crosslinking on or in close proximity to the lattice. A stent with a calcium imbibed lattice can be placed over an aneurysm neck and then one can introduce the alginate through the lattice and into the aneurysm. While flowing through the calcium imbibed lattice, the alginate can react with the calcium to cause formation of a gel in the aneurysm sac.

In FIGS. 1A and 1B, the lattice is shown to be generally uniform. Alternatively, the lattice covering can be varied along its length. For example, the size of the openings, the orientation of the openings and their shapes need not be uniform throughout the lattice covering. A portion of the lattice covering can have square-shaped openings and another portion of the lattice covering can have diamond-shaped openings.

These coverings can be joined to a stent, graft, or stent-graft over all or over only a portion of the device length. The coverings can be joined intermittently. For example, a lattice covering can be joined only at the ends of the stent, graft, or stent-graft, at the closed cell portions of the stent, or only at the closed cell connectors. The covering can be on the outside of the stent, graft, or stent-graft; it can be on the inside of the stent, graft, or stent-graft; or it can be on both.

The attachment of the lattice covering to a stent, graft, or stent-graft can be accomplished by mechanical means such as fiber, friction fit, braiding a lattice into the stent, graft, or stent-graft, or discrete mechanical attachment points (clips, etc.). The covering also can be attached by a single longitudinal strip. These components also can be bonded together through heat treatment (such as, sintering of the materials together) or through use of a wrap (for instance a tube, tape, or membrane) around the outside of the covering and stent, graft, or stent-graft (either continuous or discontinuous), that is adhered through either a thermoplastic or thermoset adhesive. The covering also can be attached to the stent, graft, or stent-graft by adhering the two together through use of a suitable adhesive. The covering can also be held in place through friction or as an interference fit. The covering can be held down at one or both ends. Combinations of these methods also can be used. These methods and combinations of these methods can be used to attach the stent and covering while under inert gas conditions as commonly known in the art.

Among suitable biocompatible adhesives are thermoplastic adhesives such as fluorinated ethylene propylene (FEP), polyurethane, cyanoacrylate, thermoplastic fluoropolymer, including flouroelastomers such as those disclosed in U.S. Pat. No. 7,049,380 [TFE/PMVE], etc. Thermoset adhesives are also useful, such as silicone including room temperature vulcanizing (RTV) silicone.

For example, where the covering is a PTFE lattice; fluorinated ethylene propylene (FEP) can be used as an adhesive. Such a coating can be applied by various methods including extrusion over the covering, powder coating with powdered FEP that is subsequently melted to flow over the lattice surface, or running the covering through a bath of molten FEP optionally followed by pulling the covering through a die to achieve uniformity of the coating. Alternatively, the stent can be provided with a coating of adhesive such as by powder coating with FEP in a continuous or discontinuous fashion, or through use of an FEP wrap (for instance a tube, tape, or membrane). In an embodiment, FEP can attach the lattice to the external surface of a stent by covering all surfaces of the stent.

A covering can be provided that allows the stent, graft, or stent-graft to be embedded within the covering material, such as through use of a silicone or other elastomeric material.

Coverings can be coextensive with the length of the stent, graft, or stent-graft, as shown in FIGS. 1A-1C and 2A-2C, or they can be either longer or shorter than the stent, graft, or stent-graft. Coverings can also cover only a portion of the stent, or can cover separately two or more portions of the stent. If multiple portions are covered, coverings can also overlap on the stent, graft, or stent-graft. For instance, one portion of the stent can be covered, while another portion remains uncovered as described in U.S. Pat. No. 6,673,102 to Vonesh et al., the entire disclosure of which is incorporated herein by reference. In one embodiment, the uncovered portion of the stent-graft in U.S. Pat. No. 6,673,102 is constrained by a lattice, wherein said lattice covered stent can be diametrically adjusted according to any one of the methods described above. Such a device allows for custom sizing of the prosthesis in order to adjust the prosthesis to a unique anatomy.

Additionally, the lattice covering and the stent, graft, or stent-graft or both can be provided with additional treatment or therapeutic agents, such as drugs, radiation, radiopaque markers or coatings, or other agents to enhance visualization in-vivo. For example, various coatings can be provided on all or some of the covering, the stent, graft, or stent-graft, or both. Suitable coating materials include fluoroelastomer, ceramic, silicone, polyethylene, carbon, gold, heparin, hydrogel, lubricious coatings, antibiotics, anticoagulant agents, anti-inflammatory agents, antimetabolic agents, antimicrobial agents, antimigratory agents, antiplatelet agents, antiproliferative agents, antisense agents, cytostatic agents, nitric oxide releasing agents, pro-endothelial agents, selective gene delivery vectors, super oxide dismutases, super oxide dismutases mimics, vasoactive agents, and combinations thereof, such as, for example, actinomycin-D, ciclosporin, clobetasol, dexamethasone, estradiol, everolimus, heparin, paclitaxel, pimecrolimus, rapamycin, sirolimus, tacrolimus, and derivatives of these compounds. Coating materials can provide numerous benefits, including protecting the underlying stent material, providing a substrate for delivery of drugs or other therapeutic substances, isolating the stent material from interaction with surrounding cells, improving fluoroscopic visualization. Coatings can be applied in any material-appropriate manner, such as dip-coating, spray-coating, electro-deposit, or chemical vapor deposition.

Such a prosthesis can be used to treat various body lumens, including, the aortoiliac, carotid, cerebral, coronary, hepatic, infrainguinal, mesenteric, renal, splenic, subclavian, and superior mesenteric arteries and veins as well as other bodily conduits such as the common bile duct, pancreatic duct, urethra intestines and colon. Such a prosthesis' configuration allows it to conform to the native anatomy of blood vessels or other body lumens, while also enhancing the stent's fatigue performance and crush-resistance.

For example, a prosthesis as described herein can be used for treating stenosis in a carotid artery of a patient. A prosthesis is provided having an insertion configuration with a reduced profile and a deployed configuration with an enlarged profile greater than the insertion profile. For example, the prosthesis can have a nitinol stent which is capable of self-expanding to the deployed configuration when a constraint is removed. The prosthesis is inserted into the vasculature of the patient. The prosthesis is then positioned and deployed within the patient's artery, for example, at a position where plaque has caused a narrowing of the artery.

The prosthesis can be implanted by a catheter delivery system or surgically (e.g. implanting a vascular graft). If the prosthesis is implanted by a catheter, the prosthesis can be radially compressed and placed within a sheath (or any constraining device). The sheath can be subsequently mounted on a 3 F to 25 F introducer-sheath compatible delivery system, depending on the prosthesis and/or the anatomy to which said prosthesis will be delivered. To aid visualization during delivery and deployment, one or more radiopaque markers can be integrated into the delivery system. For example, one radiopaque marker, such as $BaSO_4$, can be placed into the polymer used for the distal tip of the catheter. Another radiopaque marker, such as a platinum/iridium band, can be incorporated into the sheath material to indicate progression of the sheath retraction during stent deployment. Additionally, two markers, such as gold, platinum, or tantalum, can be placed adjacent to the proximal and distal ends of the compressed stent to aid in positioning.

Exemplary deployment systems that can be used in conjunction with the prosthesis disclosed herein include U.S. Pat. Nos. 6,139,572; 6,352,561 and 7,198,636 which are incorporated by reference herein.

It can be beneficial to use the disclosed coverings independently, on the stent, on the graft, or on the stent-graft hybrid. For example, a covering can provide a scaffold to reduce the risk of introduction of emboli being released into a bloodstream. A covering also can resist tissue encouragement into the lumen defined by the stent. Further, a covering can help to reduce pressure on a weakened part of a blood vessel, which in turn can reduce the risk of vessel rupture.

For example, for carotid applications, the stent with a lattice (see FIGS. 1A and 1B) can be useful for treating carotid stenosis. The lattice covered stent has flexibility and can conform to the anatomy by distending the stent and lattice to the desired size and shape of the vessel.

The method for doing so includes several steps. First, a prosthesis including a lattice and a stent is provided. Second, the prosthesis is inserted into the patient while the prosthesis is in an insertion configuration with a reduced profile. Third, the prosthesis is moved through the patient's vasculature and positioned with the portion of the carotid artery to be treated. Fourth, the prosthesis is deployed so that it assumes an enlarged profile greater than the insertion profile. Fifth, a distending pressure is applied to the stent and lattice to distend the stent to fit the anatomy of the vessel. Said distending force can be applied, for example, via a medical balloon.

In this method, the lattice and the stent are configured and positioned after deployment so that the stent provides scaffolding necessary to hold the artery open and ensure adequate blood flow, while the lattice in combination with the stent simultaneously provides the correct size and shape.

The lattice openings can further provide perfusion to a side branch vessel in this application when properly positioned. For example, a lattice can have a perfusion region with openings and an excluding region substantially without the openings. By determining the orientation of the perfusion region endovascularly, the lattice covered stent can be positioned so that the perfusion region allows side branch perfusion. Orientation can be determined by fluoroscopic visualization of one or more radiopaque markers incorporated within the lattice.

Also, a lattice covered stent can be used in conjunction with balloon catheters and/or guidewires, for example, to provide perfusion to a side branch vessel. After initially deploying the lattice covered stent as above, a balloon catheter can be endovascularly introduced into a one of the openings of the lattice, and expanded to permanently distend or disrupt the lattice covering. This allows endovascular modification of the size and shape of at least that one opening. Again, this can help to provide side branch perfusion among other uses.

Figure 14:
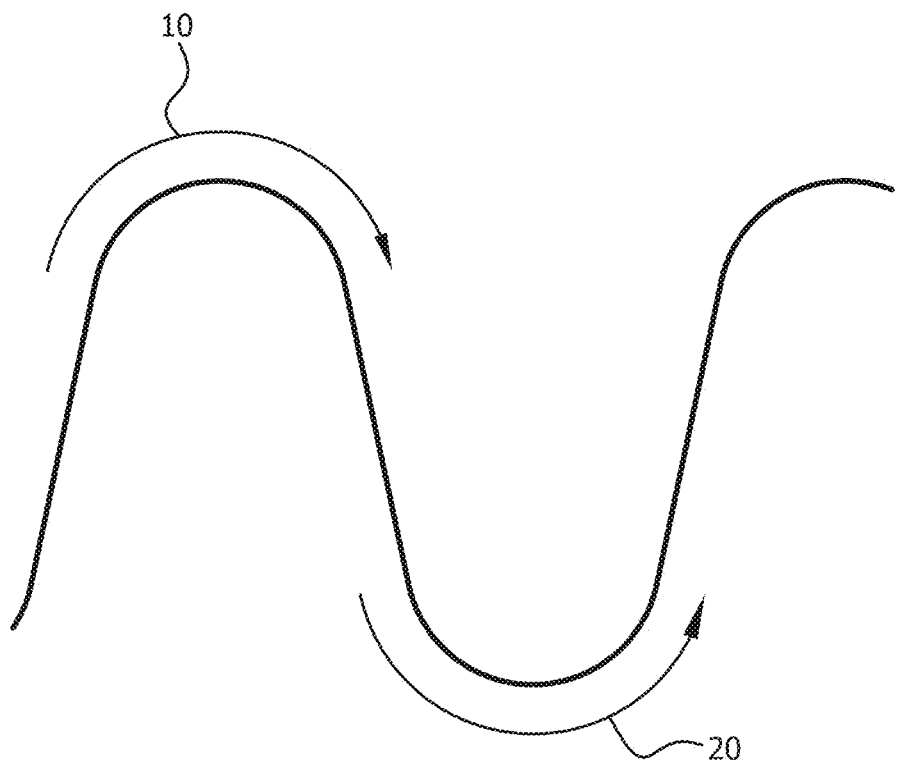
FIG. 14 is a schematic illustration of an exemplary, idealized serpentine fibril.

In another embodiment, lattice coverings comprising fluoropolymer membranes that exhibit high elongation while substantially retaining the strength properties of the fluoropolymer membrane are utilized to at least partially cover the stent, graft, or stent-graft. As discussed above, the coverings can be provided independently or on the interior or exterior surfaces of the stent, the graft, or the stent-graft. The term "elongation" or "elongated" as used herein is meant to denote the increase in length in response to the application of a tensile force. Such membranes characteristically possess serpentine fibrils, such as the idealized serpentine fibril exemplified in FIG. 14. As depicted generally in FIG. 14, a serpentine fibril curves or turns generally one way in the direction of arrow 10 then generally another way in the direction of arrow 20. It is to be understood that the amplitude and/or frequency of the serpentine-like fibrils as exemplified in FIG. 1 may vary. In one embodiment, the fluoropolymer membranes are expandable fluoropolymer membranes. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as U.S. Pat. No. 5,708,044 to Branca; U.S. Pat. No. 6,541,589 to Baillie; U.S. Pat. No. 7,531,611 to Sabol et al.; U.S. patent application Ser. No. 11/906,877 to Ford; and U.S. patent application Ser. No. 12/410,050 to Xu et al.

The high elongation is enabled by forming relatively straight fibrils into serpentine fibrils that substantially straighten upon the application of a force in a direction opposite to the compressed direction. The creation of the serpentine fibrils can be achieved through a thermally-induced controlled retraction of the expanded polytetrafluoroethylene (ePTFE), through wetting the article with a solvent, such as, but not limited to, isopropyl alcohol or Fluorinert® (a perfluorinated solvent commercially available from 3M, Inc., St. Paul, Minn.), or by a combination of these two techniques. As used herein, the term "controlled retraction" refers to causing articles to shorten in length in at least one direction by the application of heat, by wetting with a solvent, or by any other suitable means or combinations thereof in such a way as to inhibit folding, pleating, or wrinkling of the subsequent article visible to the naked eye.

The retraction of the article does not result in visible pleating, folding, or wrinkling of the ePTFE, unlike what occurs during mechanical compression. The retraction also can be applied to very thin membranes, unlike known methods. During the retraction process, the fibrils not only become serpentine in shape but also may also increase in width. Upon retraction, the expanded fluoropolymer membrane possesses serpentine fibrils. These retracted membranes characteristically possess serpentine fibrils and are wrinkle free.

The precursor materials can be biaxially expanded ePTFE membranes. In one embodiment, materials such as those made in accordance with the general teachings of U.S. Pat. No. 7,306,729 to Bacino, et al. are suitable precursor membranes, especially if small pore size articles are desired. These membranes may possess a microstructure of substantially only fibrils. In some exemplary embodiments, the membranes may possess a microstructure of substantially only serpentine fibrils. In at least one embodiment, the fluoropolymer membranes include a plurality of serpentine fibrils. As used herein, the phrase "plurality of serpentine fibrils" is meant to denote the presence of 2 or more, 5 or more, 10 or more, or 15 or more serpentine fibrils in the fluoropolymer membrane within a field of view as taught below. The serpentine fibrils have a width of about 1.0 micron or less, and in some embodiments, about 0.5 microns or less. In one embodiment, the serpentine fibrils have a width from about 0.1 to about 1.0 microns, or from about 0.1 to about 0.5 microns. The precursor membrane may or may not be amorphously locked. The precursor membrane may also be at least partially filled, coated, or otherwise combined with additional materials.

The precursor membrane may be restrained in one or more directions during the retraction process in order to prescribe the desired amount of elongation of the final article. The amount of elongation is directly related to, and determined by, the amount of retraction.

In one embodiment, retraction can be achieved in a uniaxial tenter frame by positioning the rails at a distance less than the width of the precursor membrane prior to the application of heat or solvent or both. When using a biaxial tenter frame, one or both of the sets of grips, pins, or other suitable attachment means can similarly be positioned at a distance less than the dimensions of the precursor membrane. It is to be appreciated that these retraction means differ from the mechanical compression taught by the House and Sowinski patents noted above.

The precursor membranes described above can be imbibed with an elastomeric material prior, during, or subsequent to retraction to form a composite. The term "imbibed or imbibing" as used herein is meant to describe any means for at least partially filling at least a portion of the pores of a porous material such as ePTFE or the like. The term "all or at least a portion of the pores" as used herein is meant to denote that the elastomer is present in at least a portion of all or nearly all of the pores of the ePTFE membrane. In the absence of such elastomeric materials, fluoropolymer articles having serpentine fibrils do not exhibit appreciable recovery after elongation. Suitable elastomeric materials may include, but are not limited to, PMVE-TFE (perfluoromethylvinyl ether-tetrafluoroethylene) copolymers, PAVE-TFE (perfluoro (alkyl vinyl ether)- tetrafluoroethylene) copolymers, silicones, polyurethanes, and the like. It is to be noted that PMVE-TFE and PAVE-TFE are fluoroelastomers. Other fluoroelastomers include suitable elastomeric materials as identified by those of skill in the art. The resultant retracted article possesses high elongation while substantially retaining the strength properties of the fluoropolymer membrane.

As one exemplary embodiment, a lattice of the type shown in FIGS. 1A and 2B having square-shaped openings may be prepared. It is to be understood that any shaped openings may be formed in the lattice and that square-shaped openings described herein are merely meant to be representative. To form such a lattice, a mandrel may be wrapped with an elastomeric composite material, such as the elastomeric composite material described below in Example 7. The composite material is free of wrinkles. The film-mandrel assembly may then be placed into an oven at a temperature of about 320° C. for about 12 minutes to bond the layers. After bonding, the assembly may be removed from the oven and permitted to cool at room temperature to provide an ePTFE tube. Next, a pattern of regular square openings may be cut into the ePTFE tube, such as with a $CO_2$ laser. The openings can have a size less than about 2.0 mm, about 1.0 mm, or about 0.5 mm. Additionally, the width of the lattice segments may be greater than about 0.01 mm or about 0.05 mm (see FIG. 1B). This square shaped lattice may then be placed into a convection oven at about 370° C. for approximately 12 minutes. During heating, the material shrinks to form squares that can be approximately 2.0 mm, about 1.0 mm, or about 0.5 mm, respectively, in diameter and inscribed circle and lattice segments that can be approximately 0.01 mm or approximately 0.05 mm wide, respectively. It is to be appreciated that any suitable means for attaching the elastomeric composite material to a stent or other support structure may be used and is considered to be within the scope of the invention.

A lattice made with the elastomeric composite material can be designed to be extended or elongated longitudinally or radially. In addition, the lattice may be expanded and contracted radially without creating folds which drape into the lumen. For instance, the lattice can be over-distended, such as when an over-sized catheter is placed through it, and the composite material will return (contract) without wrinkling or folding. For purposes of this invention, the entire device is considered to be "wrinkle-free" if within a 1 cm length of the device, the graft portion is devoid of wrinkles and folds when viewed by the naked eye. It is to be noted that 1 cm length of the device should be used unless the entire length of the device is less than 1 cm. In that instance, the entire device should be utilized to determine if the device is "wrinkle-free". It is to be noted that the terms "free of folds", "devoid of folds", and "fold free" are used interchangeably herein.

Once the serpentine fibrils in the elastomeric composite material are extended to a substantially straight orientation, the strength of the fluoropolymer membrane is substantially that of the original fluoropolymer membrane. Also, the elastomeric composite material can be elongated at a relatively low tensile stress until reaching a point at which a high tensile stress is required for further elongation. Further, the composite material exhibits high elongation while substantially retaining the strength properties of the fluoropolymer membrane. Additionally, with longitudinal elongation, a lattice covered stent can bend in a tight radius without the inner diameter of curvature buckling.

Further, should a stent graft be implanted undersized, no folds are present in the lattice covering. Additionally, if needed, the covered stent may be expanded beyond the nominal stent diameter. The ability of the lattice covering to remain wrinkle-free results in less or no material enfolding, which, in turn, permits the covered stent device to have a smaller profile (e.g., a reduction in delivery profile of at least 1 Fr).

Having generally described this invention, a further understanding can be obtained by reference to certain specific examples illustrated below which are provided for purposes of illustration only and are not intended to be all inclusive or limiting unless otherwise specified.

These methods of using the stent disclosed herein are exemplary and not limiting. Further uses will be recognized by a skilled artisan.

Testing Methods

It should be understood that although certain methods and equipment are described below, any method or equipment determined suitable by one of ordinary skill in the art may be alternatively utilized.

Mass, Thickness, and Density

Membrane samples are die cut to form rectangular sections about 2.54 cm by about 15.24 cm to measure the weight (using a Mettler-Toledo analytical balance model AG204) and thickness (using a Käfer Fz1000/30 snap gauge). Using these data, density is calculated with the following formula: $\rho=m/(w*l*t)$, in which: $\rho$=density (g/cm³), m=mass (g), w=width (cm), l=length (cm), and t=thickness (cm). The average of three measurements is reported.

Matrix Tensile Strength (MTS) of Membranes

Tensile break load is measured using an INSTRON 122 tensile test machine equipped with flat-faced grips and a 0.445 kN load cell. The gauge length is about 5.08 cm and the cross-head speed is about 50.8 cm/min. The sample dimensions are about 2.54 cm by about 15.24 cm. For highest strength measurements, the longer dimension of the sample is oriented in the highest strength direction. For the orthogonal MTS measurements, the larger dimension of the sample is oriented perpendicular to the highest strength direction. Each sample is weighed using a Mettler Toledo Scale Model AG204, then the thickness is measured using the Käfer FZ1000/30 snap gauge; alternatively, any suitable means for measuring thickness may be used. The samples are then tested individually on the tensile tester. Three different sections of each sample are measured. The average of the three maximum loads (i.e., peak force) measurements is reported. The longitudinal and transverse matrix tensile strengths (MTS) are calculated using the following equation: MTS=(maximum load/cross-section area)*(bulk density of PTFE)/(density of the porous membrane), where the bulk density of the PTFE is taken to be about 2.2 g/cm³.

Elongation Testing

Elongation of the retracted article can be measured by any suitable application of tensile force, such as, for example, by the use of a tensile testing machine, by hand, or by applying internal pressure to a tubular article. In the instant invention, elongation is performed at a rate of about 10% per second in all directions that are elongated. Elongation is calculated as the final length minus the initial length, divided by the initial length, and is reported as a percentage.

Scanning Electron Microscopy

Scanning electron micrographs are created choosing magnifications suitable for identifying fibrils. Articles that have been retracted in accordance with the teachings of invention may require elongation in the direction of retraction in order to identify the serpentine fibrils. For the purposes of identifying the number of serpentine fibrils, a field of view of 7 microns by 7 microns of the sample is to be employed.

In addition, for the purpose of characterizing fibril width, measurements should be made for serpentine fibrils that are substantially separated from each other and do not band together or otherwise form series of fibrils paralleling each other within the membrane. To determine the fibril width, a line is drawn through the SEM image to bisect it. The SEM image should be of sufficient magnification such that at least 5 serpentine fibrils and not more than 20 serpentine fibrils are clearly visible within the SEM image. Starting from one edge of the bisected image, the width of the first five consecutive serpentine fibrils that intersect the bisecting line are measured. The measurements are made where the fibril intersects the bisecting line. Next, the five measurements are averaged and the average measurement is recorded.

Removal of Elastomer from a Lattice Material

For lattice materials containing elastomer, the elastomer can be dissolved or degraded and rinsed away using an appropriate solvent in order to measure or examine desired properties.

For instance, the fluoroelastomer component of a lattice material can be partially or substantially removed to enable SEM imaging of the ePTFE structure. The samples are submerged in 95 g of Fluorinert Electronic Liquid FC-72 (3M Inc., St. Paul, Minn.) and allowed to soak without agitation. After approximately one hour, the fluorinated solvent is poured off and replaced with 95 g of fresh solvent. This process is repeated for a total of 5 soaking cycles, the first 4 cycles for approximately 1 hour, and the 5th cycle for approximately 24 hours. Alternatively, to aid in the removal of elastomer, the sample can also be agitated using an ultrasonic cleaner (e.g. Branson 200 Ultrasonic Cleaner (Model—B200)).

EXAMPLES

Example 1

A lattice of the type shown in FIGS. 1A and 2B with square-shaped openings is prepared. A mandrel is wrapped with an ePTFE film with a discontinuous FEP coating to a thickness of approximately 0.05 mm. The film-mandrel assembly is placed into an oven at 320° C. for 12 minutes to bond the layers. The assembly is removed from the oven and allowed to cool at room temperature to provide an ePTFE tube. Using a $CO_2$ laser, a pattern of regular square openings is cut into the tube. The openings are square-shaped with a size of less than about 0.5 mm. The width of the lattice segments is greater than about 0.05 mm (see FIG. 1B). The prepared square shaped lattice is placed in a convection oven set at 370° C. for 12 minutes. The material shrinks during heating to form squares that are approximately 0.5 mm diameter inscribed circle and lattice segments that are approximately 0.05 mm wide.

Example 2

A lattice of the type shown in FIGS. 1B and 2C with diamond-shaped openings is prepared. An oversized mandrel that is approximately 25% larger than the nominal stent diameter is wrapped with an ePTFE film with a discontinuous FEP coating to a thickness of approximately 0.05 mm.

The film-mandrel assembly is placed into an oven at 320° C. for 12 minutes to bond the layers. The assembly is removed from the oven and allowed to cool at room temperature to provide an ePTFE tube. Using a $CO_2$ laser, a pattern of slits approximately 40% longer than the final inscribed circle diameter are oriented transverse to the longitudinal axis of the mandrel are cut into the tube. The tube with slits is removed from the mandrel and tensioned over the nominal stent diameter mandrel and the slits open to form diamond shapes. The tube ends are temporarily fixed to length on the mandrel by ePTFE tape. The assembly is then placed into a convection oven set at 370° C. for 12 minutes. The material shrinks to form diamonds that are approximately 0.5 mm diameter inscribed circle and lattice segments are approximately 0.05 mm wide.

Example 3

A stent is powder coated with a thin layer of FEP powder (DuPont® FEP Fluoropolymer Resin, Product Type 5101) in a tabletop blender within which the stent is suspended. After the stent is placed within the blender with FEP powder, the blender is activated. The powder disperses into the volume of the blender chamber and the stent is powder coated. After approximately 3 seconds, the stent is removed, and is placed into a convection oven set at 320° C. for 5 minutes. After this time, the stent is removed and allowed to air cool.

The stent is then placed on a mandrel having an outer diameter approximately equal to the inner diameter of the stent. The mandrel is covered on its outer diameter with polyimide film. To temporarily fix the stent to the mandrel, the stent is placed in a convection oven set at 320° C. for 4 minutes.

After removal from the oven and cooling of the stent and mandrel assembly, a square-shaped opening lattice according to Example 1 is coaxially positioned over the stent.

The lattice is axially tensioned over the stent and comes in full contact with the outer diameter of the stent. The covering ends are temporarily fixed to length on the mandrel by ePTFE tape. A temporary layer of ePTFE film is then tightly wrapped around the assembly. The perforated covering is then placed within a convection oven set at 320° C. oven for 12 minutes to adhere the covering to the stent. After removal from the oven and being allowed to cool to ambient temperature, the temporary film wrapping is removed, and the stent and lattice covering are removed from the mandrel. The lattice is then trimmed flush with the end of the stent.

Example 4

The stent is powder coated as described in Example 3 above. The prepared diamond-shaped opening lattice of Example 2 is coaxially positioned over the stent. The lattice is axially tensioned over the stent, causing it to decrease in diameter and to come in full contact with the outer diameter of the stent. The lattice ends are temporarily fixed to length on the mandrel by ePTFE tape. A temporary layer of ePTFE film is then tightly wrapped around the assembly. The lattice is then placed within a convection oven set at 320° C. oven for 12 minutes. After removal from the oven and being allowed to cool to ambient temperature, the temporary film wrapping is removed, and the stent and lattice covering are removed from the mandrel. The lattice is then trimmed flush with the end of the stent.

Example 5

A lattice of the type shown in FIGS. 5A-5C and 6A-6C with square-shaped openings and varied length segments is prepared. A mandrel is wrapped with an ePTFE film with a discontinuous FEP coating to a thickness of approximately 0.05 mm. The film-mandrel assembly is placed into an oven at 320° C. for 12 minutes to bond the layers. The assembly is removed from the oven and allowed to cool at room temperature to provide an ePTFE tube. Using a $CO_2$ laser, (1) a pattern of irregular parallelogram openings is cut into the tube (see FIGS. 5A and 6A). The openings are shaped to provide segments with no excess length or with some excess length, e.g., segment with no bends, one bend, or two bends. The openings have a size of less than about 0.5 mm in one dimension and less than about 0.17 mm in the second dimension. The width of the lattice segments is greater than about 0.05 mm (see FIG. 1B). The prepared lattice is placed in a convection oven set at 370° C. for 12 minutes. The material shrinks during heating to form parallelograms with or without excess length that are approximately 0.5 mm in the long dimension and 0.17 in the short dimension and lattice segments that are approximately 0.05 mm wide.

Example 6

A drug-eluting lattice of the type shown in FIGS. 9A and 10 with square-shaped openings is prepared. A mandrel is wrapped with an ePTFE film with a discontinuous FEP coating to a thickness of approximately 0.05 mm with at least one reservoir layer comprising a therapeutic agent. Using a $CO_2$ laser, a pattern of regular square openings is cut into the tube. During laser cutting, the FEP used in manufacture of a multi-layer lattice, reflows and seals the inner walls of the openings holding the therapeutic agent within the reservoir layer. The openings are square-shaped with a size of less than about 0.5 mm. The prepared square shaped lattice is placed in a convection oven set at 370° C. for 12 minutes. The material shrinks during heating to form squares that are approximately 0.5 mm diameter inscribed circle and lattice segments that are approximately 0.05 mm wide.

Example 7

An exemplary elastomeric composite material was made in the following manner.

Precursor Membrane

A biaxially expanded ePTFE membrane that had been amorphously locked and had the following properties was obtained: thickness=0.002 mm, density=0.837 g/cc, matrix tensile strength in the strongest direction=475 MPa, matrix tensile strength in the direction orthogonal to the strongest direction=390 MPa, elongation at maximum load in the strongest direction=68%, and elongation at maximum load in the direction orthogonal to the strongest direction=86%. Upon tensioning by hand, the membrane did not noticeably retract upon the release of the tension.

Retracted Membrane

A roll of precursor membrane, wherein the length direction corresponded with the weakest direction of the membrane, was restrained in the clamps of a heated, uniaxial tenter frame and fed into the heated chamber of the tenter frame. The oven temperature was set to about 270° C. The rails of the tenter frame within the heated chamber were angled inward in order to allow membrane shrinkage to about 39% of its original width in response to the heat. The line speed was set to provide a dwell time of about 1.5 minutes within the heated chamber.

The initial and final widths of the membrane were 1625 mm and 632 mm, respectively. The retracted membrane had the following properties: thickness=0.003 mm, density=1.36 g/cc, matrix tensile strength in the strongest direction of the precursor membrane=158 MPa, matrix tensile strength in the direction orthogonal to the strongest direction of the precursor membrane=409 MPa, elongation at maximum load in strongest direction of the precursor membrane=301%, and elongation at maximum load in the direction orthogonal to the strongest direction of the precursor membrane=85%.

Extruded Elastomer

A copolymer comprising tetrafluoroethylene (TFE) and perfluoro(methyl vinylether) (PMVE) as described in U.S. Pat. No. 7,049,380 to Chang, et al. was obtained with a PMVE/TFE ratio of 2:1. The copolymer was extruded at about 350° C. into a thin film. The film had the following properties: thickness=0.025 mm and width=115 mm.

Elastomeric Composite Material

The extruded elastomer was fed onto the surface of the retracted membrane and spooled with a 0.064 mm thick high density polyethylene release film. The elastomeric composite material had the following properties: thickness=0.033 mm and width=115 mm.

Figure 15:
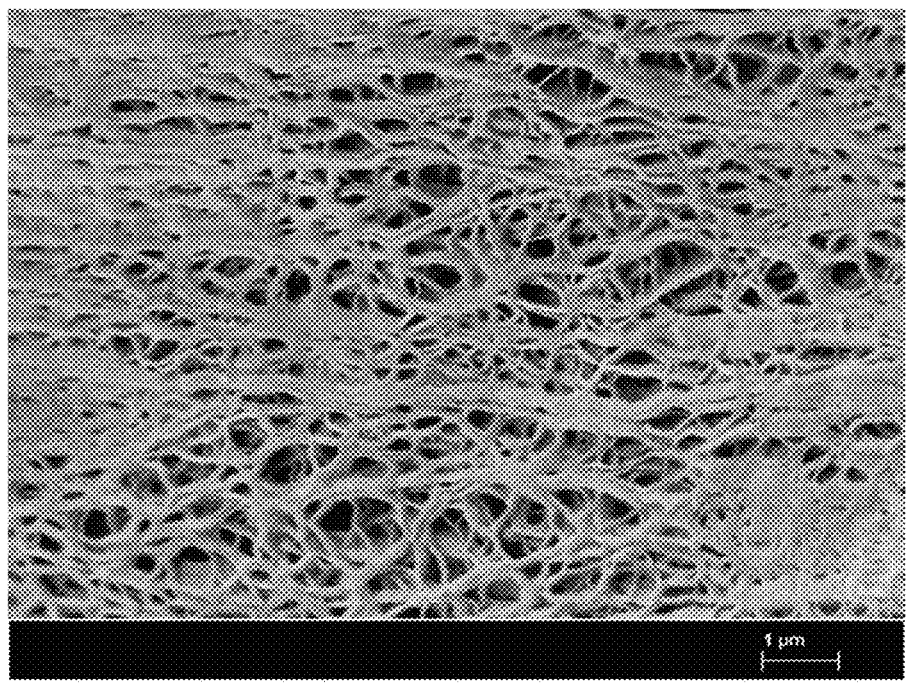
FIG. 15 is a scanning electron micrograph of the surface of an elastomeric composite material with the copolymer removed.

The fibrils of the membrane were noted to have a serpentine shape as shown in FIG. 15, a scanning electron micrograph of the surface of an elastomeric composite material with the copolymer removed taken at 10,000×.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An endoprosthesis including a stent structure and a graft structure, the endoprosthesis having a collapsed state and an expanded state, the endoprosthesis in the expanded state comprising:
a first end portion expanded to a first diameter and having a first resistance to further diametric expansion at the first diameter;
a second end portion expanded to a second diameter and having a second resistance to further diametric expansion at the second diameter; and
an intermediate portion arranged between the first end portion and the second end portion and being expanded to a third diameter that is less than at least one of the first diameter and the second diameter, the intermediate portion having a third resistance to diametric expansion at the third diameter that is less than at least one of the first and second resistances to further diametric expansion of the first and second end portions, respectively and being diametrically adjustable to a fourth diameter that is greater than the third diameter upon application of an expansion force to the intermediate portion and remain at the fourth diameter and maintain the third diameter in the absence of the expansion force.

2. The endoprosthesis of claim 1, wherein the third diameter that is less than both the first diameter and the second diameter.

3. The endoprosthesis of claim 1, wherein the first end portion, the second end portion, and the intermediate portion form at least one of a dog bone shape, an hour glass shape, and a tapered shape.

4. The endoprosthesis of claim 1, wherein both the first and second resistances to further diametric expansion are greater than the third resistance to further diametric expansion.

5. The endoprosthesis of claim 1, wherein the third resistance to further diametric expansion is greater than a physiological pressure range of a vessel.

6. The endoprosthesis of claim 1, wherein the intermediate portion is constrained by a lattice structure.

7. The endoprosthesis of claim 1, wherein the stent structure is arranged with the first end portion, the second end portion, and the intermediate portion, and the stent structure is self-expanding.

8. The endoprosthesis of claim 1, wherein the stent structure extends beyond one of the first end portion and the second end portion.

9. An endoprosthesis including a self-expanding stent structure and a graft structure, the endoprosthesis having a collapsed state and an expanded state, the endoprosthesis in the expanded state comprising:
a first end portion expanded to a first diameter;
a second end portion expanded to a second diameter; and
an intermediate portion arranged between the first end portion and the second end portion and being expanded to a third diameter that is less than the first diameter and the second diameter such that the endoprosthesis defines at least one of a dog-bone, an hourglass, or a tapered shape, the intermediate portion being diametrically adjustable to a fourth diameter that is greater than the third diameter upon application of an expansion force to the intermediate portion and remain at the fourth diameter and maintain the third diameter in the absence of the expansion force.

10. The endoprosthesis of claim 9, wherein the third diameter that is less than both the first diameter and the second diameter.

11. The endoprosthesis of claim 9, wherein the intermediate portion is constrained at the third diameter by a lattice structure.

12. The endoprosthesis of claim 9, wherein the stent structure is arranged with the first end portion, the second end portion, and the intermediate portion.

13. The endoprosthesis of claim 9, wherein the stent structure extends beyond one of the first end portion and the second end portion.

14. An endoprosthesis comprising:
a mid-section constrained by a lattice structure including a plurality of openings and being diametrically adjustable from a deployed diameter to a larger diameter upon application of an expansion force to the mid-section and remain at the larger diameter and maintain the deployed diameter in the absence of the expansion force;
a proximal end; and
a distal end;
each of the proximal and distal ends being expanded relative to the mid-section such that the endoprosthesis retains a dog bone shape that is resistant to dilation and creep.

15. The endoprosthesis of claim 14, wherein the lattice structure is configured to expand in at least one of a sloped and a stepped manner.

16. The endoprosthesis of claim 15, wherein the plurality of openings in the lattice have a size between about 10 μm and about 40 μm.

17. The endoprosthesis of claim 14, further comprising a stent structure is arranged with the proximal end, the distal end, and the mid-section, and the stent structure is self-expanding.

\* \* \* \* \*